US011110144B2

(12) United States Patent
Lu et al.

(10) Patent No.: US 11,110,144 B2
(45) Date of Patent: Sep. 7, 2021

(54) WOLFBERRY GLYCOPEPTIDE COMPOSITION AND METHODS FOR PREPARING AND USING THE SAME

(71) Applicant: Shanghai Institute of Organic Chemistry, Chinese Academy of Sciences, Shanghai (CN)

(72) Inventors: Long Lu, Shanghai (CN); Yan Jiang, Shanghai (CN); Juan Shen, Shanghai (CN); Zhigang Ding, Shanghai (CN); Yuhua Xiang, Shanghai (CN); Guiqing Chen, Shanghai (CN); Gengyuan Tian, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 60 days.

(21) Appl. No.: 16/049,238

(22) Filed: Jul. 30, 2018

(65) Prior Publication Data
US 2020/0030403 A1   Jan. 30, 2020

(51) Int. Cl.
| | |
|---|---|
| *A61K 36/815* | (2006.01) |
| *B01D 21/26* | (2006.01) |
| *B01D 61/14* | (2006.01) |
| *A23L 33/18* | (2016.01) |
| *A23L 33/105* | (2016.01) |
| *A61K 38/16* | (2006.01) |
| *A61K 8/64* | (2006.01) |
| *A61K 8/9789* | (2017.01) |
| *A61Q 19/00* | (2006.01) |
| *A61Q 19/08* | (2006.01) |
| *A61P 35/00* | (2006.01) |
| *A61P 37/00* | (2006.01) |
| *A61P 3/06* | (2006.01) |
| *A61P 9/00* | (2006.01) |

(52) U.S. Cl.
CPC .......... *A61K 36/815* (2013.01); *A23L 33/105* (2016.08); *A23L 33/18* (2016.08); *A61K 8/645* (2013.01); *A61K 8/9789* (2017.08); *A61K 38/168* (2013.01); *A61P 3/06* (2018.01); *A61P 9/00* (2018.01); *A61P 35/00* (2018.01); *A61P 37/00* (2018.01); *A61Q 19/00* (2013.01); *A61Q 19/08* (2013.01); *B01D 21/262* (2013.01); *B01D 61/145* (2013.01); *A23V 2002/00* (2013.01); *A61K 2236/331* (2013.01); *A61K 2236/39* (2013.01); *A61K 2236/51* (2013.01)

(58) Field of Classification Search
CPC .................................................. A61K 36/815
See application file for complete search history.

(56) References Cited

FOREIGN PATENT DOCUMENTS

| CN | 1258512 A | * | 7/2000 |
|---|---|---|---|
| CN | 1068792 C | | 7/2001 |
| CN | 107021995 A | * | 8/2017 |
| CN | 107021995 A | | 8/2017 |

OTHER PUBLICATIONS

Huang, Linjuan et al., "Isolation, purification and physico-chemical properties of immunoactive constituents from the fruits of *Lycium barbarum* L."Acta Pharmaceutica Sinica, 33(7): 512-516 (1998).
Zhang Weijie, "Biochemical Research Technology of Sugar Complex," pp. 12-13 and 112-116, Zhejiang University Press (1994).
National Standard in China, GB/T 22427/10, "Determination of nitrogen content of starch and its derivatives,".
Wang Baikun, "Immunological pharmacological action of wolfberry polysaccharide on T, killing T and NK cells and the counteraction of immunosuppressive action on cyclophosphamide," Chinese Journal of Pharmacology and Toxicology, No. 4, pp. 39-43, (1990).
Huang, Linjuan et al., "Studies on the glycoconjugates and glycans from *Lycium barbarum* L. in inhibiting low density lipoprotein (LDL) peroxidation," Acta Pharmaceutica Sinica, 36(2):108-111 (2001).
Tian, Gengyuan, "Study on structure and bioactivity of glycoconjugate compounds of fructus *Lycii*," World Science and Technology, 5(4) (2003).
Huang, Linjuan and Tian, Gengyuan, "Structure elucidation and immunoactivity studies of glycan of glycoconjugate Lbgp4 isolated from the fruit of *Lycium barbarum* L.," Chemical Journal of Chinese Univ., vol. 3,pp. 407-411 (2001).
Tian, Gengyuan et al., "Structure elucidation of a high MW glycan of a glycoprotein isolated from the fruit of *Lycium barbarum* L.," Acta Biochmica et Biophysica sinica, 27:5, pp. 493-498 (1995).
Tian, Gengyuan et al., "Isolation, purification and properties of LbGp and characterization of its glycan-peptide bond," Acta Biochmica et Biophysica sinica, 27:2, pp. 201-206 (1995).
Qi, Chunhui et al., "Chemical structure and immunoactivity of the glycoconjugates and their glycan chains from the fruit of *Lycium barbarum* L.," Chinese Journal of Pharmacology and Toxicology, Jun. 15:3; pp. 185-190 (2001).
Peng, Xuemei et al., "Physico-chemical properties and activity of glycoconjugate LbGP2 from Lycium barbarum L.," Acta Pharmaceutica sinica, 36(8): 599-602 (2001).

(Continued)

*Primary Examiner* — Amy L Clark
(74) *Attorney, Agent, or Firm* — Mei & Mark LLP; Manni Li

(57) ABSTRACT

Wolfberry glycopeptide composition and methods for preparing and using the same, the part with a molecular weight distribution of 1000 Da to 10000 Da of the wolfberry glycopeptide accounts for 50-85% on the HPLC differential refractive index map; and the protein content is 20-35% weight percentage, neutral polysaccharide content is 20-35% weight percentage. Optionally, the uronic acid content is 5-20% weight percentage. The preparation method of the present invention removes part of insoluble impurities by a heating flocculation method, instead of the conventional organic solvent extraction process, and without using any organic solvents in the whole process.

11 Claims, 17 Drawing Sheets

(56) References Cited

OTHER PUBLICATIONS

Xu, Shunlin et al., "Effect of *Lycium barbarum* L. glycopeptide on the intracellular free calcium concentration of cardiomyocytes in neonatal hypoxia mice," Chinese Journal of Clinical Rehabilitation, vol. 9: (11), pp. 62-65 (Mar. 21, 2005).

Xu, Shunlin et al., "Effects of LbGP on the intracellular free calcium concentration of cardiomyocytes induced by hypoxia and KCl," China Journal of Chinese Materia Medica, vol. 30(7): 534-538 (Apr. 2005).

Qi, Chunhui et al., "Immunoactivity of the crude polysaccharides from the fruit of *Lycium barbarum* L.," Chinese Journal of Pharmacology and Toxicology, Jun.: 15(3): 180-184 (2001).

Huang, Linjuan et al., "Structure elucidation of glycan of glycoconjugate lbgp3 isolated from the fruit of *Lycium barbarum* L.," Journal of Asian Natural Products Research, vol. 1: 259-267 (2006).

Peng, Xuemei et al., "Studies on chemistry and immuno-modulating mechanism of a glycoconjugate from *Lycium barbarum* L. ,"Chinese Journal of Chemistry, 19: 1190-1197 (2001).

Peng, Xuemei et al., "Physico-chemical properties and bioactivities of a glycoconjugate LbGp5B from *Lycium barbarum* L.," Chinese Journal of Chemistry, 19: 842-846 (2001).

Peng, Xuemei et al., "Structural characterization of the glycan part of glycoconjugate LbGp2 from *Lycium barbarum* L.," Carbonhydrate Research 331: 95-99 (2001).

\* cited by examiner

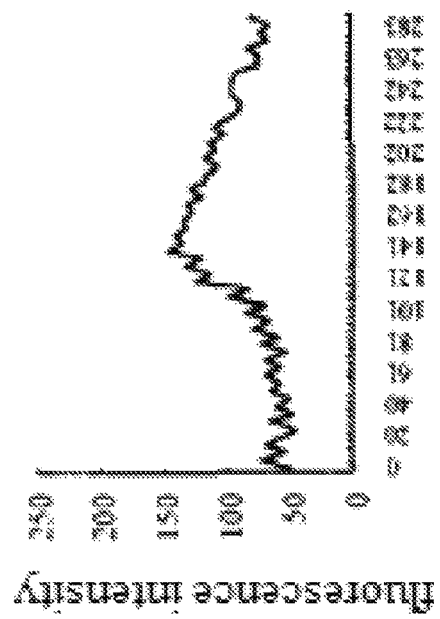
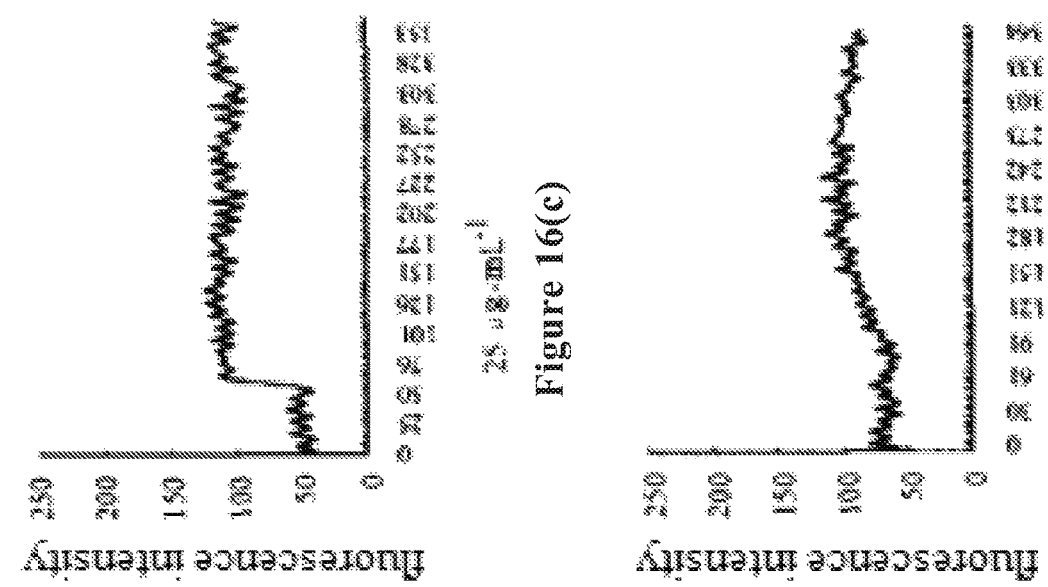
Figure 16(c)
Figure 16(d)
Figure 16(e)

WOLFBERRY GLYCOPEPTIDE COMPOSITION AND METHODS FOR PREPARING AND USING THE SAME

TECHNICAL FIELD

The present invention relates to medical science and technology, in particular, wolfberry glycopeptide composition and methods for preparing and using the same for preparing immuno-enhancement medicine, health care products, food, and daily chemical products.

BACKGROUND ART

*Lycium barbarum* L. or *Lycium chinense* Mill. is the mature fruit of plant wolfberry of *Solanaceae Lycium* that possesses various health benefits and has been approved as food with dual function of medicine and nutrition by the Ministry of Health in China. In the English speaking countries, wolfberry is generally known or referred to as "*lycium*," "barbary wolfberry," "Chinese wolfberry," "matrimony vine," "goji," or "goji berry." Wild wolfberry may survive in cold sandy areas ranging from 6,000 to 9,000 feet above the sea level, such as in the provinces of Qinghai, Inner Mongolia, and Shaanxi in China, and it is widely planted in Ningxia. Species of Wolfberry exist in a wide range of geographical areas including Iran, India, North Africa, Southeast Europe, the Mediterranean, and United States, and survive in the form of spontaneous and ornamental plants.

Wolfberry contains various active ingredients, among which, small molecules include carotene/carotenoid, thiamine, riboflavine, nicotinic acid, ascorbic acid, b-sitosterol, zeaxanthin, physalien, betaine, and β-cryptoxanthin; and macromolecules include dietary fibers, wolfberry polysaccharides, proteins, and fats.

Traditional methods for extracting the active ingredients of wolfberry mostly involve cooking at high temperature and deproteinization by the Sevage method. The active ingredients in the wolfberry, such as polysaccharides, are destroyed during the process and thus rarely reported.

Polysaccharide is a polyhydroxy aldehyde or ketone that is soluble in water. Water extraction and alcohol precipitation is the most commonly used method for extracting polysaccharides. In the traditional extraction method, an organic solvent, such as ethanol, is added to an aqueous solution containing the polysaccharides to destroy hydrogen bonds in the aqueous solution, thereby reducing the solubility of the polysaccharides in water and allowing polysaccharides to precipitate and separated from water. Solvents commonly used for alcohol precipitation are ethanol and acetone. However, organic solvents have safety concern on explosion and require solvent recovery during the production process. Thus, simple, environmentally friendly, and safe method for extraction and production in lieu of the alcohol precipitation is in need and has great application prospects.

SUMMARY OF THE INVENTION

The present invention provides a novel and environmentally friendly method for preparing a novel glycopeptide composition from wolfberry without organic solvent extraction or precipitation.

The method of the present invention comprises the steps of soaking fruit of wolfberry in water to form a liquid mixture, and centrifuging the liquid mixture to remove precipitated solids and to obtain a first extract solution; heating the first extract solution to form a flocculation in the first extract solution, and centrifuging the first extract solution to remove the flocculation and to obtain a second extract solution having a light transmittance at 50% or higher at 400 nm; and treating the second extract solution with an ultrafiltration membrane, taking a cut-off solution, and concentrating and drying the cut-off solution to obtain a glycopeptide composition. The flocculation in the first extract solution is formed by agglomerating insoluble substance in the first extract solution into precipitates. The molecular weight cutoff of the ultrafiltration membrane is in a range of 1000 Da to 2000 Da.

In the present invention, the fruit of wolfberry may be soaked in water at a temperature in a range of 10° C. to 35° C. for a time period of 2 hours to 10 hours. The first extract solution may be heated at a temperature in a range of 45° C. to 70° C. for 0.5 hour to 5 hours to form the flocculation.

In the present invention, the mass ratio of the fruits of wolfberry to the amount of water for soaking is 1:1 to 1:15. The fruits of wolfberry may be dried or fresh fruits. When the fruits of wolfberry are dried fruits, preferably, the mass ratio of the dried fruits to the amount of the water for soaking is 1:5 to 1:15; when the fruits of wolfberry are fresh fruits, preferably, the mass ratio of the fresh fruits to the amount of water for soaking is 1:1 to 1:3.

In the present invention, the step of centrifuging to obtain the first extract solution is conducted at a centrifugal speed in a range of 1000 rpm to 4000 rpm, and time for centrifuge is 10 seconds to 1 minute.

In the present invention, preferably, the light transmittance of the second extract solution is at 60% or more at 400 nm.

In the present invention, the first extract solution is heated to 45° C. to 70° C. for 0.5 hour to 5 hours, and centrifuged at a centrifugal speed in a range of 6000 rpm to 16000 rpm for a time period of 5 seconds to 5 minutes.

In the present invention, the cut-off solution is dried by freeze drying, spray drying, or both, to obtain the glycopeptide composition.

Further, the present invention comprises the steps of continuously supplementing water to the cut-off solution during the ultrafiltration, while monitoring an electrical conductivity and a sugar degree of the cut-off solution. The cut-off solution is collected when the electrical conductivity of the cut-off solution is below 1000 us/cm and the sugar degree is below 1.2.

The present invention also provides a glycopeptide composition for use as an immuno-enhancement medicine, health care products, food, or daily chemical product, as prepared by the method of the present invention. The glycopeptide composition of the present invention has a molecular weight distribution that molecules having molecular weight in the range of 1000 Da to 10000 Da account for 50-85% of the molecules on the HPLC differential refractive index map.

In the glycopeptide composition of the present invention, the protein content is at about 20-35% weight percentage, and neutral polysaccharide content is at about 20-35% weight percentage. Further, the uronic acid contents in the glycopeptide composition of the present invention may be at about 5-20% weight percentage.

The present invention further provides a method for using the glycopeptide composition of the present invention, comprising the step of administering to a subject in need of a treatment the glycopeptide composition of the present invention at an effective dose at 1 to 500 mg per unit.

The present invention further provides a pharmaceutical composition comprising the glycopeptide composition of the present invention and a pharmaceutically acceptable carrier. The pharmaceutical composition is used for enhancing immunity, anti-tumor, anti-radiation, treating chronic hepatitis B, treating fatty liver, tumor adjuvant therapy, and anti-aging. The pharmaceutically acceptable carrier may be an anti-adherent, a binder, a coating, a coloring agent, a disintegrant, a filler, a flow agent, flavors, a glidant, a lubricant, a preservative, a sorbent, a sweetener, a vehicle, or a sustained release agent.

The present invention further provides a nutriceutical or food composition for improving physical condition and enhancing immunity, comprising the glycopeptide composition of the present invention and optionally a food additive, a nutrient, an herbal extract, or a pharmaceutical ingredient.

The present invention further provides a cosmetic or daily chemical composition comprising the glycopeptide composition of present invention and an additive. The cosmetic or daily chemical composition is in the form of mask, lotion, serum, cleanser, ointment, cream, spray, aqueous solution, or oil product. The additive may be a an emulsifier, a skin moisturizer, a humectants, olive oil, glycerin, a stabilizer, water, or a mixture thereof.

BRIEF DESCRIPTION OF DRAWINGS

FIG. 16 shows the fluorescence intensity curve of dynamic intracellular calcium in the experimental groups in Example 23, where FIG. 16(c) shows the result in the group pretreated with the wolfberry glycopeptide composition of the present invention at 25 µg/mL, FIG. 16(d) shows the result in the group pretreated with the wolfberry glycopeptide composition of the present invention at 50 µg/mL, and FIG. 16(e) shows the result in the group pretreated with the wolfberry glycopeptide composition of the present invention at 100 µg/mL.

DETAILED DESCRIPTION OF THE INVENTION AND EMBODIMENTS

Figure 1:
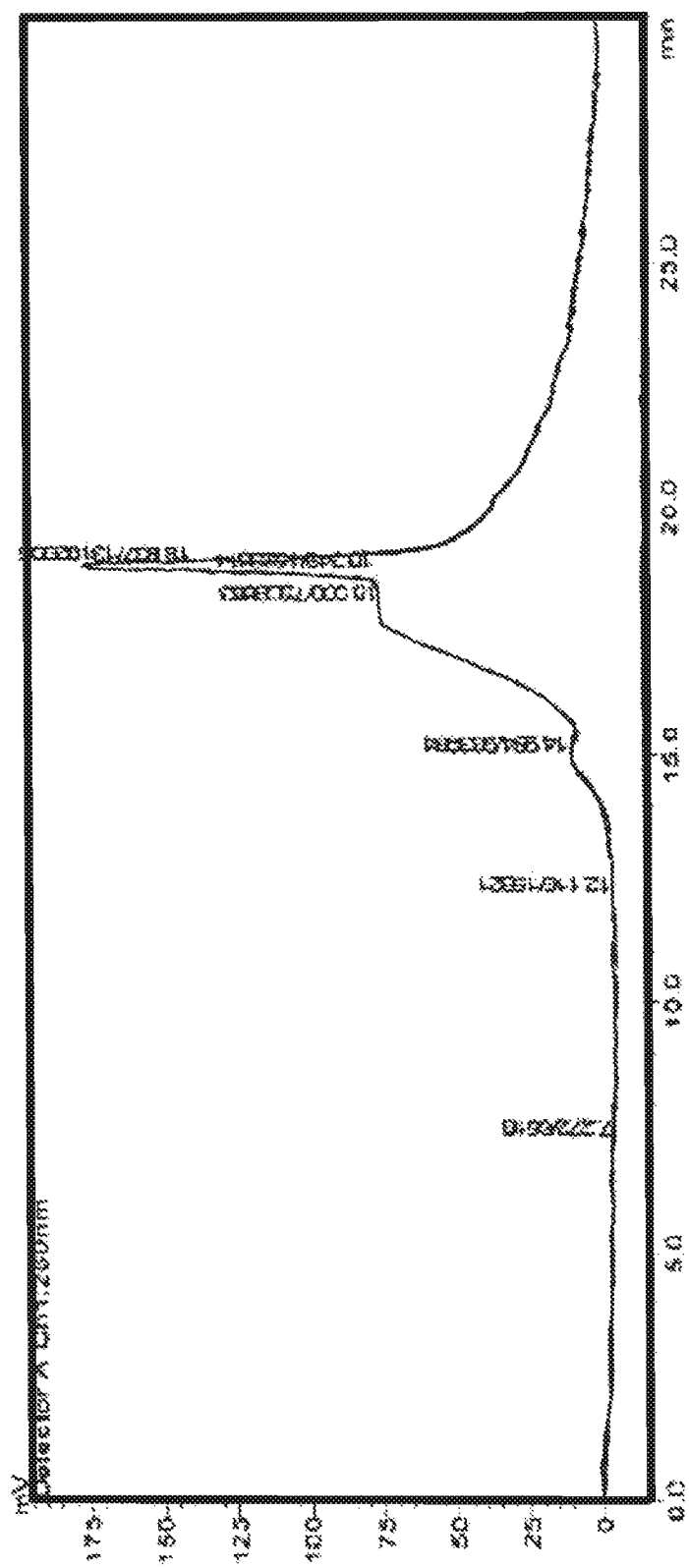
FIG. 1 shows an HPLC ultraviolet spectrum of the wolfberry glycopeptide composition of the present invention as prepared in Example 1.

The method of the present invention for preparing the wolfberry glycopeptide composition comprises the following steps:

(a) soaking the fruit of wolfberry in water and centrifuging to remove precipitated solids, thereby obtaining a first extract solution;

(b) heating the first extract solution, agglomerating the insoluble substance in the first extract solution into precipitates in the form of a flocculation, and centrifuging to remove the flocculation, thereby obtaining a second extract solution;

(c) separating the second extract solution with an ultrafiltration membrane, taking a cut-off solution, and concentrating and drying the cut-off solution to obtain a wolfberry glycopeptide.

In the present invention, the fruits of wolfberry may be dried fruits, fresh fruits, or both. The mass ratio of the fruits to the amount of the water is 1:1 to 1:15. Preferably, the mass ratio of the dried fruits to the amount of the water is 1:5 to 1:15, and the mass ratio of the fresh fruits to the water is 1:1 to 1:3.

In the present invention, the fruits of wolfberry may be crushed before soaking. Preferably, the fruits may be soaked in deionized water. The first extract solution may be a turbid aqueous extract. The step of soaking in water is conducted at a temperature in a range of 10° C. to 35° C. The time for soaking is 2 hours to 10 hours.

In present invention, the step of centrifuging to obtain the first extract solution is conducted at a centrifugal speed in a range of 1000 rpm to 4000 rpm, and the time for centrifuge is 10 seconds to 1 minute.

In the present invention, the second extract solution is a clear solution, and the transmittance of the second extract solution is about 50% or more, and preferably at 60% or more, at 400 nm as measured by a UV-visible spectrophotometer. It is important for the second extract solution to achieve the transmittance as required, which ensures that the flocculation formed from the congregation of insoluble substances are properly removed and the process may go foreword with the next step of ultrafiltration. If the second extract solution does not achieve the required clarify, then, the ultrafiltration membrane may get clogged by the insoluble substances and the entire process may not proceed successfully.

Preferably, in step (b), the first extract solution is heated to 45° C. to 70° C. for 0.5 hour to 5 hours, and centrifugal speed is 6000 rpm to 16000 rpm, and centrifugal time is 5 seconds to 5 minutes.

In the present invention, the drying step may by conducted by freeze drying and spray drying. During the step of separation with ultrafiltration membrane, deionized water is continuously added to the cut-off solution, the electrical conductivity and sugar degree of the cut-off solution is being monitored. When the electrical conductivity of the cut-off solution falls below 1000 us/cm as measured by an conductivity meter, and the sugar degree falls below 1.2 as measured by a Brix meter, the separation with ultrafiltration process may be ended, and the cut-off solution is collected, concentrated, and dried to form the wolfberry polypeptide composition of the present invention. The molecular weight cutoff of the ultrafiltration membrane is in the range of 1000 Da to 2000 Da.

The present invention further provides a wolfberry glycopeptide composition with excellent pharmacological activity. The wolfberry glycopeptide composition of the present invention has molecular weight distribution that those macromolecules having molecular weight in the range of 1000 Da to 10000 Da account for at least 50%, and preferably, in the range of 50-85% of the composition as shown on the HPLC differential refractive index map. Method for determination of the molecular weight distribution is known in the art and may be accomplished by suitable equipment, for example, Shimadzu RID-10A.

The macromolecules in the wolfberry glycopeptide composition of the present invention are mostly glycopeptides having the structure of glyco-conjugates, where a glycan chain is linked to a peptide via an ortho-glucosidic bond, as determined by Thin Layer Chromatography (TLC). The detection method is known, for example, as disclosed in Huang, Linjuan, et al., "Study on the isolation, purification and physicochemical properties of the immuno-reactive components in wolfberry," Acta Pharmaceutica Sinica 1998, 33(7): 512-516. The contents of the article is incorporated herein by reference.

The wolfberry composition of the present invention has the protein content at about 20-35% weight percentage (calculated from and based on the weight percentage of nitrogen (N) element at 3.2-5.6% weight percentage in the composition) and the neutral polysaccharide content at about 20-35% weight percentage. Further, the wolfberry composition may contain uronic acid content at about 5-20% weight percentage. The wolfberry glycopeptide composition of the present invention has a slightly lower content of neutral sugar than the products obtained by conventional methods, while the contents of the uronic acid and protein are significantly improved and higher.

The present invention further provides a method for using the wolfberry glycopeptide composition for preparing immuno-enhancing medicine, health care products, food, or daily chemical products. The wolfberry glycopeptide composition may be used for preparing medicine, nutritional and health products, or food, which is provided in a manner suitable for absorption by the human body. The present invention further provides a wolfberry glycopeptide product comprising the wolfberry glycopeptide composition of the present invention.

For examples, the wolfberry glycopeptide composition of the present invention may be mixed with known drug carriers, nutriceutical excipients, pharmaceutical excipients, food ingredients, dietary supplement ingredients, and food additives to form capsules, tablets, caplets, liquids, tableting, etc. In the finished product, the content of the wolfberry glycopeptide composition of the present invention is 1 mg to 500 mg per unit, preferably 10 mg to 120 mg per unit, more preferably 25 mg to 100 mg per unit. Known drug carriers and excipients include, but are not limited to, anti-adherent, binder, coating, colors, disintegrants, fillers, flavors, glidants, flow agents, lubricants, preservatives, sorbents, sweeteners, vehicles, sustained release agents, etc. For example, silicone oxide, magnesium stearate, microcrystalline cellulose, pregelatinized starch, etc. Known food additives include, but are not limited to, preservatives, flavoring agents, food colorings, etc. For example, citric acid, mannitol, etc. Further, the wolfberry glycopeptide composition of the present invention can be mixed with other nutrients and herbal medicines or pharmaceutical ingredients to fully exert its efficacy and synergistic effects. For example, a cranberry extract, a pine mushroom, a blueberry extract, a grape seed extract, a cooked lotus seed powder, a maca powder, a *ginseng*, etc.

The wolfberry glycopeptide composition of the present invention may be mixed with known cosmetic and daily chemical additives for preparing cosmetic and skin care product, which is absorbed and utilized by the human body in a manner of acting on the surface of the human skin. Such products include masks, lotions, cleansers, ointments, serum, creams, sprays, aqueous solutions, oil products, etc. Daily chemical additives include, but are not limited to, moisturizers, humectants, stabilizers, emulsifiers, etc. For example, the wolfberry glycopeptide obtained by the present invention can be mixed with high melting point fatty compounds, such as emulsifiers, skin moisturizers, humectants, olive oil, glycerin, stabilizers, water, additives, or a mixture of the above to obtain a product with a suitable texture.

The method for preparing the wolfberry glycopeptide composition of the present invention has resulted from extensive and in-depth study and a large number of screening and testing over a long period of time. Greatly improved from the traditional water extraction method, the method of the present invention promotes self-flocculation of the insoluble substance by the heating step and uses centrifuge to remove flocculated impurities. The method does not use any organic solvents for extraction and precipitation, and separates and extracts wolfberry glycopeptide by pure physical method, thereby avoiding use of any organic solvents which poses safety risks and problem of solvent recovery and environmental pollution.

Further, as it involves no use of organic solvents, the explosion-proof requirements are reduced as well as the industrial wastes. The process is easy to operate with improved safety, and is more green and environmentally friendly with greatly reduced production cost.

Moreover, the method of the present invention significantly increases the percentage of the glycopeptide component having a molecular weight of 1000 Da to 10000 Da in the product, improves the yield of the final glycopeptide product, and the activity of the glycopeptide product remains unchanged. The method and product of the present invention show great potential for market promotion and application.

The following pharmacological examples show the immuno-enhancing, anti-tumor, and antioxidant activities of the wolfberry glycopeptide composition of the present invention. The level of T lymphocyte and B lymphocyte proliferation is significantly improved after administration of the wolfberry glycopeptide composition of the present invention, and which has a significant immunological activity.

The present invention is further illustrated below in the following examples. It should be understood that these examples are for illustrating the present invention but do not limit the scope of the present invention.

The experimental methods with no specific conditions described in the following examples are generally performed under the conventional conditions, or according to the manufacturer's instructions. Unless indicated otherwise, parts and percentage are weight parts and weight percentage.

Experimental Methods and Instruments:

The main instruments and methods used in the preparation process of the wolfberry glycopeptide composition of the present invention are: CR22G centrifuge; N4S UV-visible spectrophotometer; 1812 ultrafiltration device; DDSJ-318 conductivity meter; PAL-1 Brix meter.

The detection methods used in the present invention are conventional. The detection method for sugar contents or saccharide is known, for example, at Zhang Weijie, "Biochemical Research Technology of Sugar Complex," pages 12-13 and 112-116, Zhejiang University Press (1994), the contents of which is incorporated herein by reference.

For the mass detection of wolfberry glycopeptide, the molecular weight distribution of wolfberry glycopeptide is determined by Gel Permeation Chromatography (GPC): chromatographical column TSK gel G3000 7.8*300 mm, mobile phase 50 mM $Na_2PO_4$ (pH 6.8) 0.5 ml/min. The HPLC spectrum are produced by Shimadzu LC-20A; and HPLC differential refractive index maps are produced by Shimadzu RID-10A. The molecular weight distribution on the HPLC differential refractive index map, is measured or calculated by linear equation of logarithm of molecular weight and retention time.

The polysaccharide content is determined by anthrone-sulfuric acid method: a standard solution is prepared using reference glucose, and anthrone-sulfuric acid is used for color development. The standard curve is made by taking the absorbance as ordinate and the sugar degree as abscissa. The wolfberry glycopeptide sample is also colored with anthrone-sulfuric acid. The absorbance value is measured and taken into the standard curve to convert the sample concentration and calculate the sugar degree, and the result is multiplied by a polysaccharide correction coefficient of 0.91.

Determination of uronic acid content: a standard solution is prepared with reference glucose uronic acid, and carbazole-sulfuric acid is used for color development. The standard curve is made by taking the absorbance as ordinate and the sugar degree as abscissa. The wolfberry glycopeptide sample is also colored with carbazole-sulfuric acid. The absorbance value is measured and taken into the standard curve to convert the sample concentration and calculate the uronic acid content.

The nitrogen content of the wolfberry glycopeptide is determined by the elemental analysis method as defined in the National Standard in China, GB/T 22427/10, "Determination of nitrogen content of starch and its derivatives," contents of which is incorporated herein by reference.

Example 1. Preparing the Glycopeptide Composition of the Present Invention with Dried Fruits Dried fruits of wolfberry 100 g is smashed and soaked in deionized water. The amount of deionized water for soaking is at a mass ratio of 15 times to the amount of dried fruits, and the soaking is conducted at 10° C. for 10 hours. Then, the soaking liquid is placed in a CR22G centrifuge and centrifuged at 1000 rpm for 1 minute, and the supernatant obtained by centrifugation is observed to be turbid.

The supernatant is placed in a water bath and heated to 40° C. for 5 hours. The pulp and pectin remained in the supernatant congregate to a flocculation. The liquid containing the congregated flocculation is placed in a CR22G centrifuge and centrifuged at 16,000 rpm for 5 seconds, and a clear solution is obtained. The light transmittance of the clear solution at 400 nm is 83% as measured by an N4S UV-visible spectrophotometer.

The clear solution is placed in an 1812 ultrafiltration device for ultrafiltration. The molecular weight cutoff of the ultrafiltration membrane is 1000 Da and the working pressure is 5 kg. Deionized water is continuously supplemented to the cut-off solution during ultrafiltration. The change of conductivity is monitored online by DDSJ-318 conductivity meter and real-time change in sugar degree is monitored by PAL-1 Brix meter. When the conductivity of the cut-off solution is decreased to 500 us/cm and the sugar degree is decreased to 0.7, the solution containing a macromolecular portion cut-off by the ultrafiltration membrane is collected, concentrated, and freeze-dried to obtain 0.85 g of wolfberry glycopeptide composition of the present invention.

Figure 2:
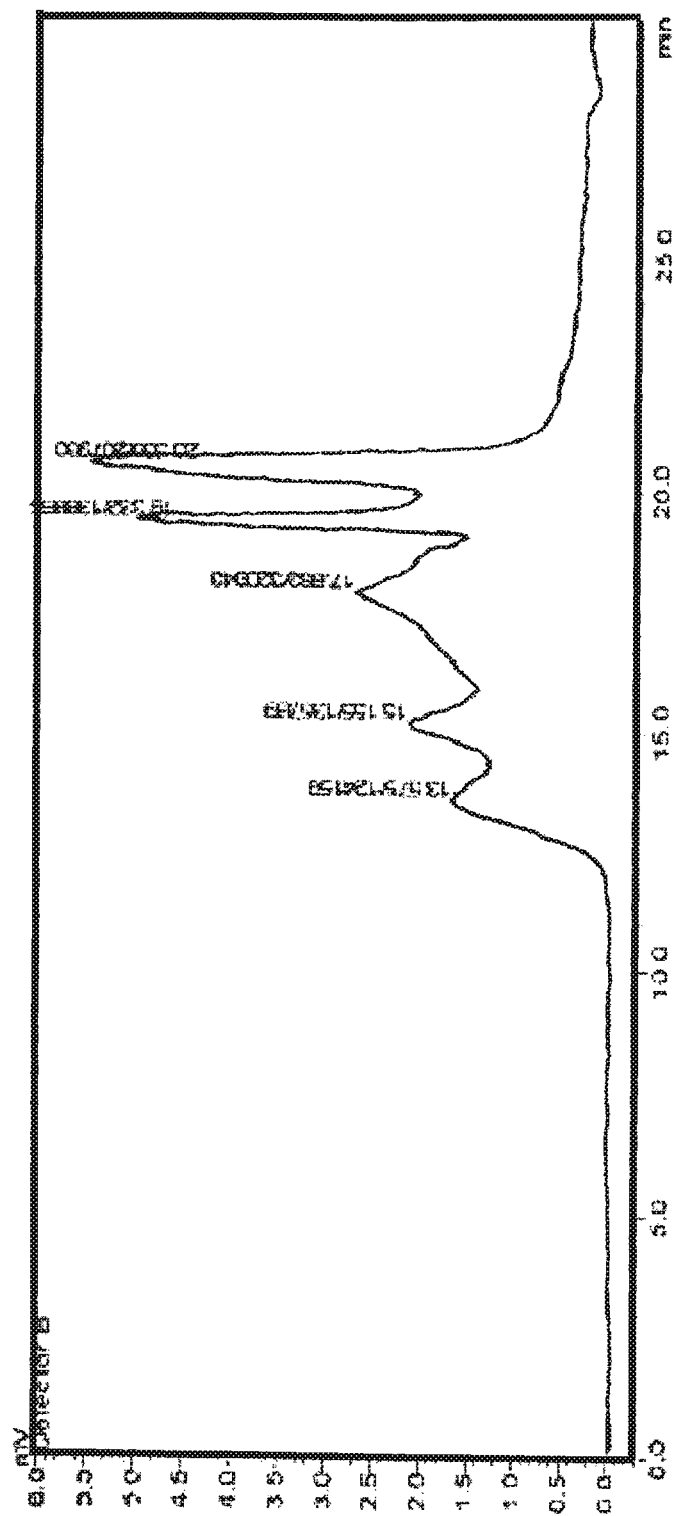
FIG. 2 shows an HPLC differential refractive index map of the wolfberry glycopeptide composition of the present invention as prepared in Example 1.

The wolfberry glycopeptide product is analyzed by HPLC. The portion with a molecular weight of 1000-10000 Da accounts for 80% in the product; the protein content is at 35% weight percentage as determined by the Kjeldahl method, neutral polysaccharide content is at 20% weight percentage as determined by the anthrone-sulfuric acid method, and uronic acid content is at 20% weight percentage as determined by carbazole method. FIG. 1 shows the HPLC ultraviolet spectrum, and FIG. 2 shows the HPLC differential refractive index map of the wolfberry glycopeptide.

Example 2. Preparing Glycopeptide Composition of the Present Invention with Dried Fruits Dried fruits of wolfberry 100 g is smashed and soaked in deionized water. The amount of the deionized water is at a mass ratio of 10 times to the amount of the dried fruits, and the soaking is conducted at 20° C. for 5 hours. The soaking liquid is placed in a CR22G centrifuge and centrifuged at 4000 rpm for 10 seconds, and the supernatant obtained by centrifugation is observed to be still turbid.

The supernatant is placed in a water bath and heated at 60° C. for 2 hours. The pulp and pectin remained in the supernatant congregate to a flocculation. The liquid is placed in a CR22G centrifuge and centrifuged at 13,000 rpm for 5 minutes to obtain a clear solution with a light transmittance of 78%.

Next, the clear solution is placed in an ultrafiltration device for ultrafiltration. The molecular weight cutoff of the ultrafiltration membrane is 1000 Da and the working pressure is 5 kg. Deionized water is continuously supplemented to the cut-off solution. When the conductivity of the cut-off solution is decreased to 900 us/cm and the sugar degree to 1.0, the solution containing macromolecular portion cut-off by the ultrafiltration membrane is collected, concentrated, and freeze-dried to obtain 1.1 g wolfberry glycopeptide.

Figure 3:
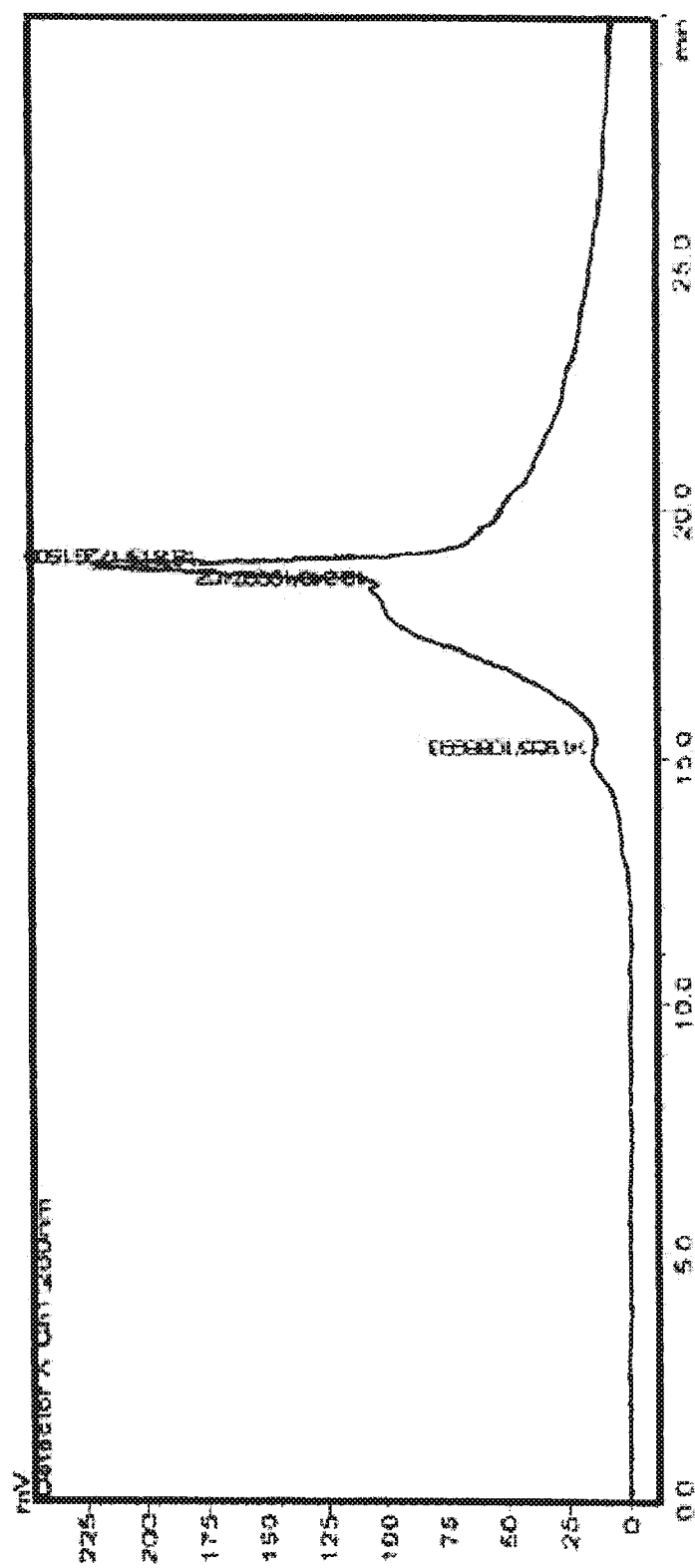
FIG. 3 shows an HPLC ultraviolet spectrum of the wolfberry glycopeptide composition of the present invention as prepared in Example 2.
Figure 4:
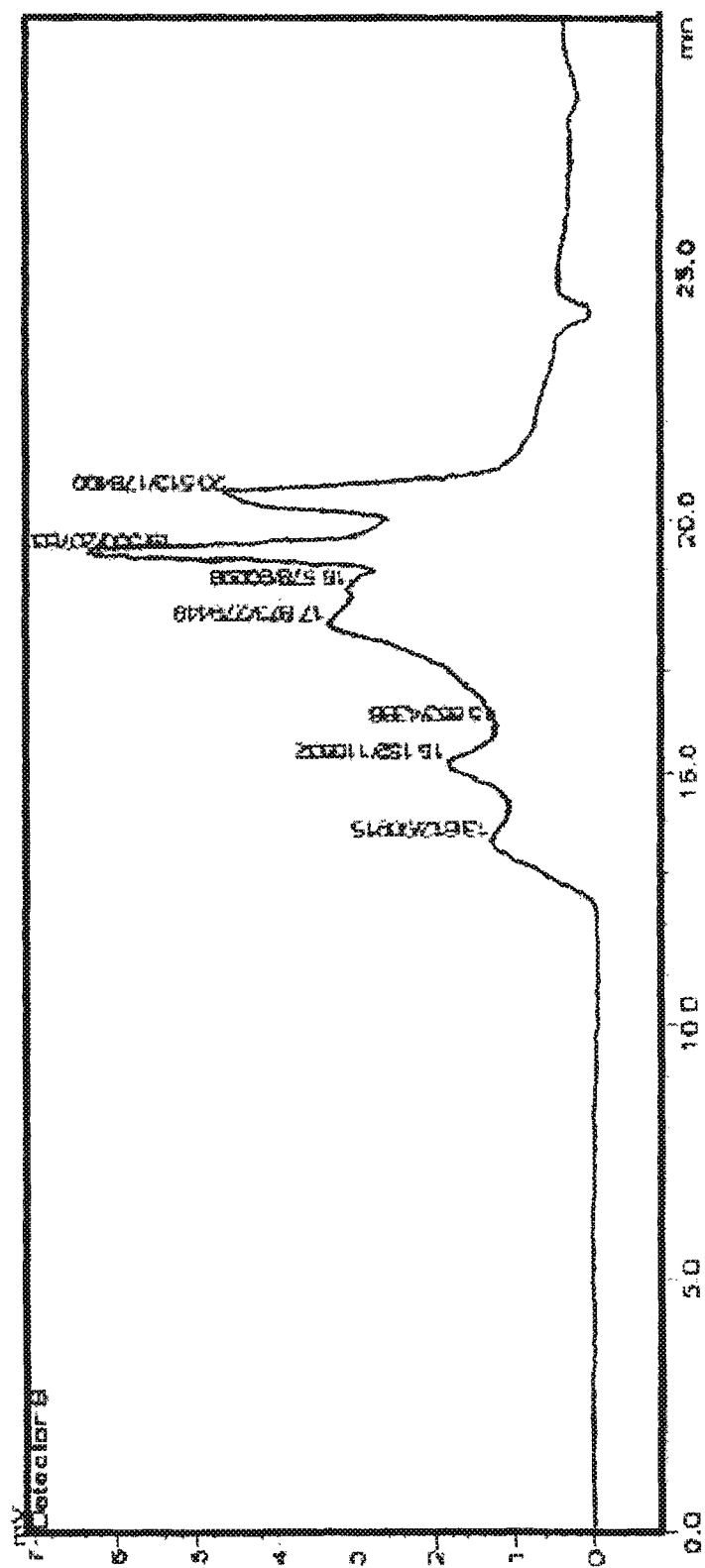
FIG. 4 shows an HPLC differential refractive index map of the wolfberry glycopeptide composition of the present invention as prepared in Example 2.

The wolfberry glycopeptide is analyzed by HPLC and determined that the part with a molecular weight of 1000-10000 Da accounts for 60%; the protein content is at 30% weight percentage as determined by the Kjeldahl method, the neutral polysaccharide content is at 25% weight percentage as determined by anthrone-sulfuric acid method, and uronic acid content is at 10% weight percentage as determined by carbazole method. FIG. 3 shows the HPLC ultraviolet spectrum, and FIG. 4 shows the HPLC differential refractive index map of the wolfberry glycopeptide.

Example 3. Preparing Glycopeptide with Dried Fruits

Dried fruit of wolfberry 100 g is smashed and soaked in deionized water. The amount of deionized water is at a mass ratio of 5 times to the amount of dried fruits, and soaking is conducted at 30° C. for 2 hours. The soaking liquid is then transferred to a CR22G centrifuge and centrifuged at 3000 rpm for 1 minute to obtain a supernatant that is observed to be still turbid.

The supernatant is placed in a water bath and heated to 70° C. for 0.5 hours. The pulp and pectin remained in the supernatant congregate to a flocculation. The liquid is placed in a CR22G centrifuge and centrifuged at 6000 rpm for 5 minutes to obtain a clear solution with a light transmittance of 60%.

Next, the clear solution is placed in an ultrafiltration device for ultrafiltration. The molecular weight cutoff of the ultrafiltration membrane is 2000 Da, and the working pressure is 5 kg. Deionized water is continuously supplemented to the cut-off solution. When the conductivity of the cut-off solution is decreased to 300 us/cm and the sugar degree to 0.6, the solution containing macromolecular portion cut-off is collected, concentrated, and freeze-dried to obtain 0.8 g of wolfberry glycopeptide.

Figure 5:
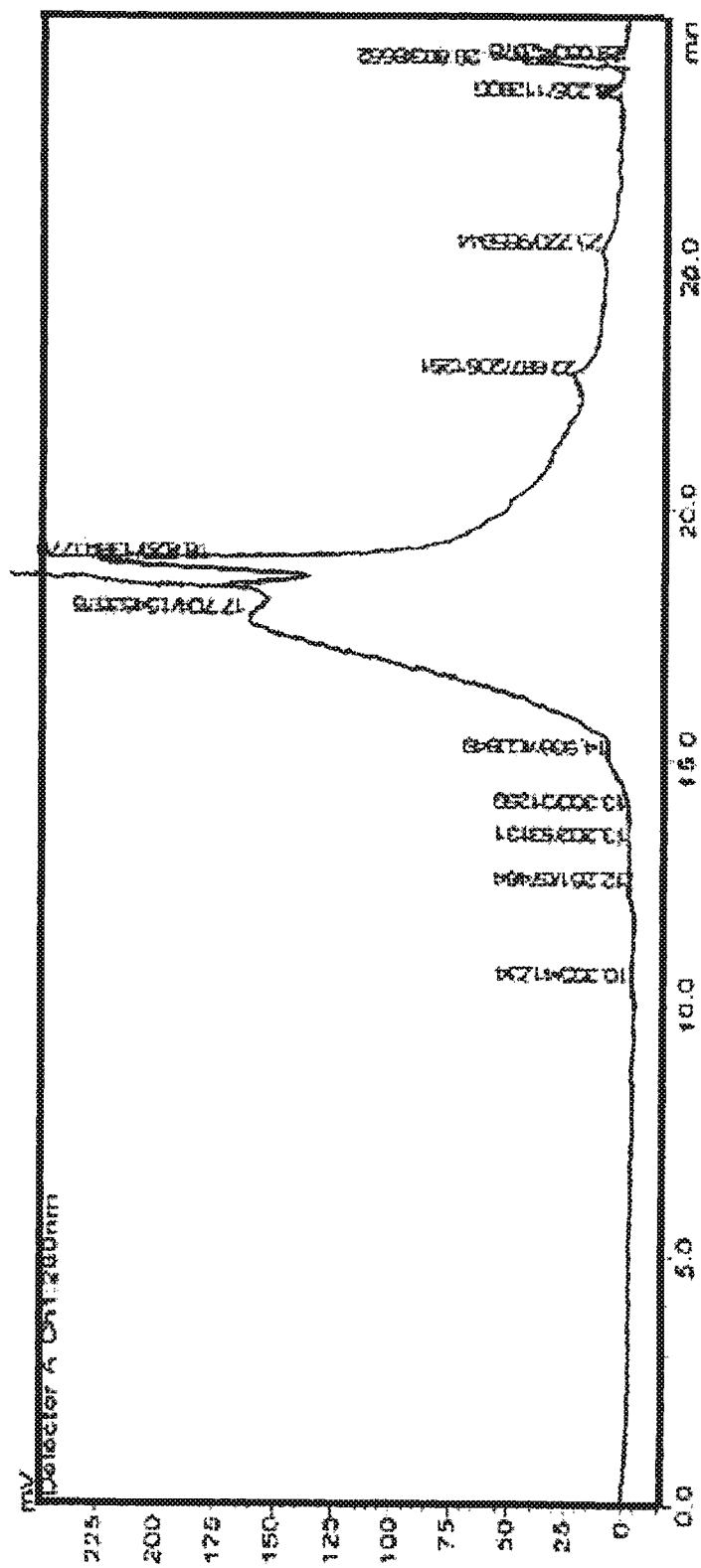
FIG. 5 shows an HPLC ultraviolet spectrum of the wolfberry glycopeptide composition of the present invention as prepared in Example 3.
Figure 6:
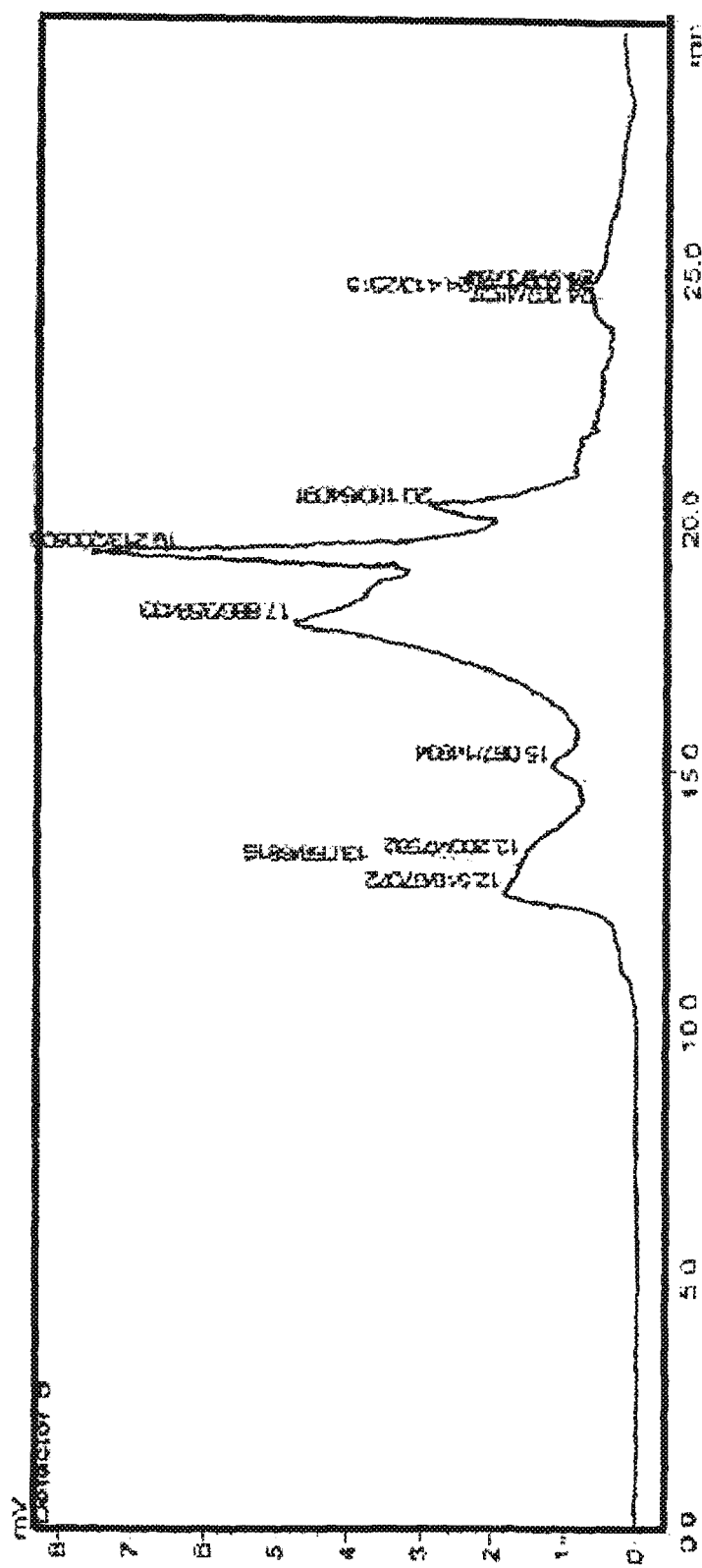
FIG. 6 shows an HPLC differential refractive index map of the wolfberry glycopeptide composition of the present invention as prepared in Example 3.

The wolfberry glycopeptide is analyzed by HPLC and determined that the part with a molecular weight of 1000-10000 Da accounts for 85%; the protein content is at 20% weight percentage as determined by the Kjeldahl method, the neutral polysaccharide content is at 35% weight percentage as determined by anthrone-sulfuric acid method, and uronic acid content is at 5% weight percentage as determined by carbazole method. FIG. 5 shows the HPLC ultraviolet spectrum, and FIG. 6 shows the HPLC differential refractive index map of the wolfberry glycopeptide.

Example 4. Preparing Wolfberry Glycopeptide Composition of the Present Invention with Fresh Fruits Fresh fruit of wolfberry 400 g is smashed and soaked in a deionized water at a mass ratio of 1 time to the amount of fresh fruits. The soaking is conducted at 10° C. for 10 hours. The soaking liquid is centrifuged in a CR22G centrifuge at 4000 rpm for 1 minute to obtain a supernatant that is observed to be still turbid.

The supernatant is placed in a water bath and heated to 40° C. for 3 hours. The pulp and pectin remained in the supernatant congregate to a flocculation. The liquid is placed in a CR22G centrifuge and centrifuged at 10000 rpm for 0.5 minutes to obtain a clear solution with a light transmittance of 67%.

The clear solution is placed in an ultrafiltration device for ultrafiltration. The molecular weight cutoff of the ultrafiltration membrane is 1000 Da, and the working pressure is 5 kg. Deionized water is continuously supplemented to the cut-off solution. When the conductivity of the cut-off solution is decreased to 1000 us/cm and the sugar degree to 1.2, and the solution containing macromolecular portion cut off is collected, concentrated, and freeze-dried to obtain 1.1 g wolfberry glycopeptide.

Figure 7:
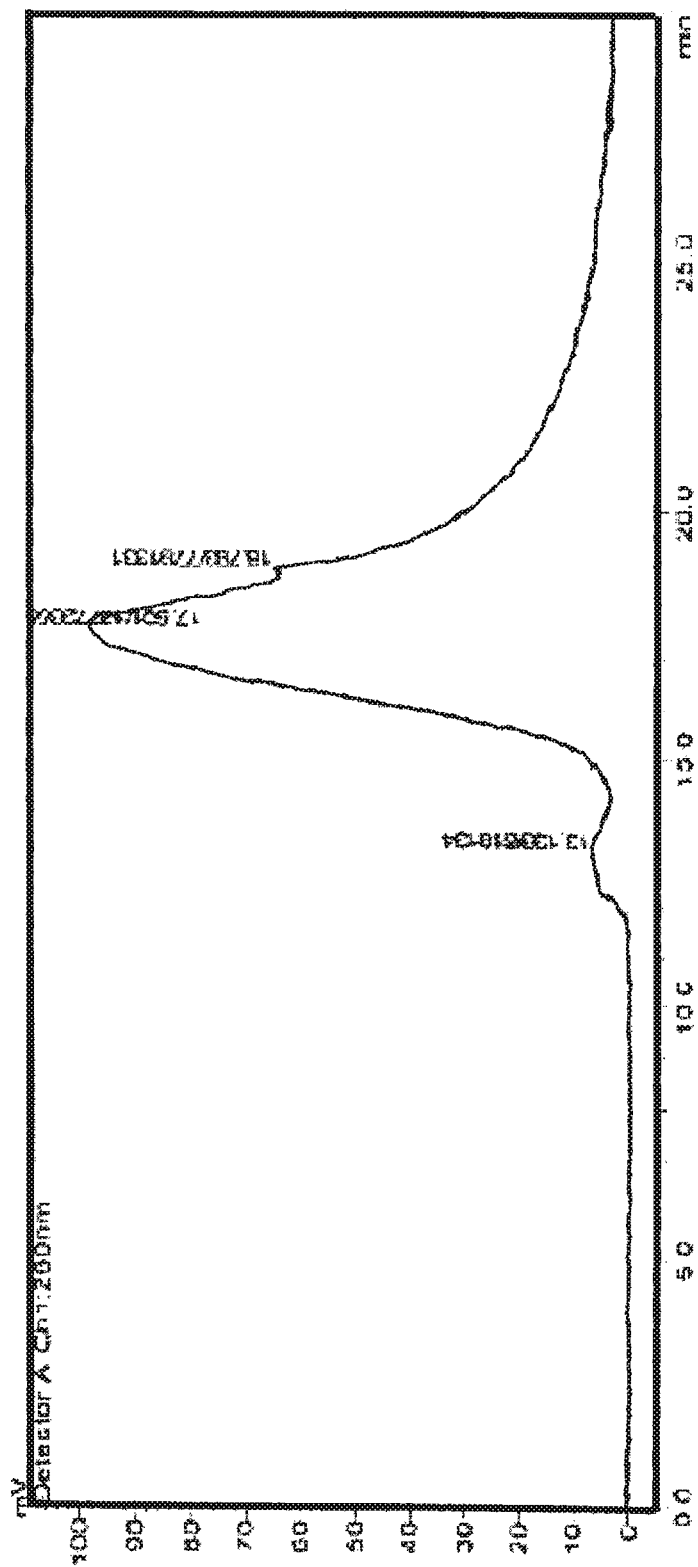
FIG. 7 shows an HPLC ultraviolet spectrum of the wolfberry glycopeptide composition of the present invention as prepared in Example 4.
Figure 8:
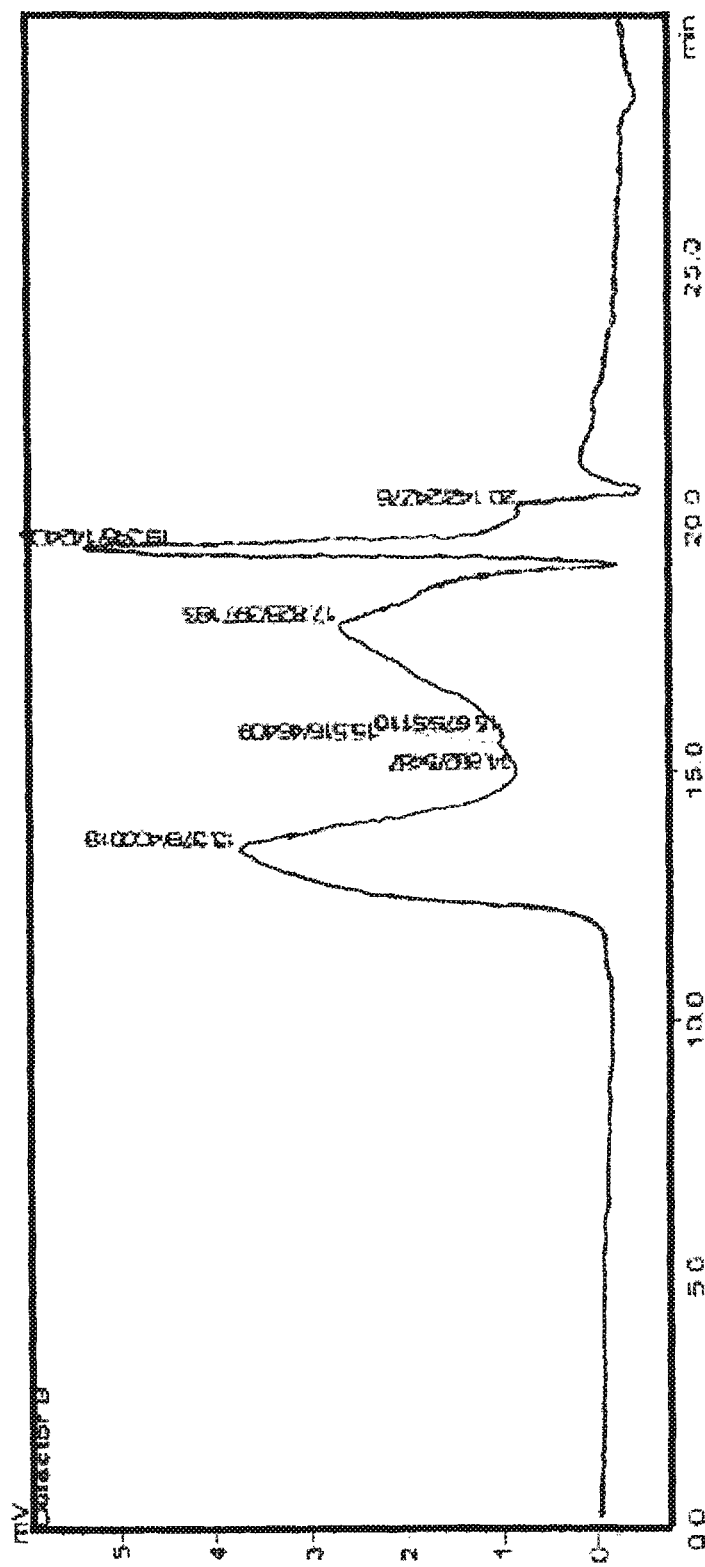
FIG. 8 shows an HPLC differential refractive index map of the wolfberry glycopeptide composition of the present invention as prepared in Example 4.

The wolfberry glycopeptide is analyzed by HPLC and determined that the part with a molecular weight of 1000-10000 Da accounts for 50%; the protein content is at 20% weight percentage as determined by Kjeldahl method, the neutral polysaccharide content is at 35% weight percentage as determined by anthrone-sulfuric acid method, and uronic acid content is at 10% weight percentage as determined by carbazole method. FIG. 7 shows the HPLC ultraviolet spectrum, and FIG. 8 shows the HPLC differential refractive index map of the wolfberry glycopeptide.

Example 5. Preparing Glycopeptide Composition of the Present Invention with Fresh Fruits Fresh fruits of wolfberry 400 g is smashed and soaked in deionized water. The amount of deionized water is at a mass ratio of 2 times to that of fresh fruits, and soaking is conducted at 20° C. for 5 hours. The soaking liquid is placed in a CR22G centrifuge and centrifuged at 1000 rpm for 1 minute to obtain a supernatant that is still cloudy.

The supernatant is placed in a water bath and heated to 50° C. for 1.5 hours. The pulp and pectin remained in the supernatant congregate to a flocculation. The liquid is placed in a CR22G centrifuge and centrifuged at 11,000 rpm for 20 seconds to obtain a clear solution with a light transmittance of 73%.

The clear solution is placed in an ultrafiltration device for ultrafiltration. The molecular weight cutoff of the ultrafiltration membrane is 2000 Da, and the working pressure is 5 kg. Deionized water is continuously supplemented to the cut-off solution. When the conductivity of the cut-off solution is decreased to 900 us/cm and the sugar degree to 0.9, the solution containing macromolecular portion cut-off is collected, concentrated, and freeze-dried to obtain 1.0 g wolfberry glycopeptide.

Figure 9:
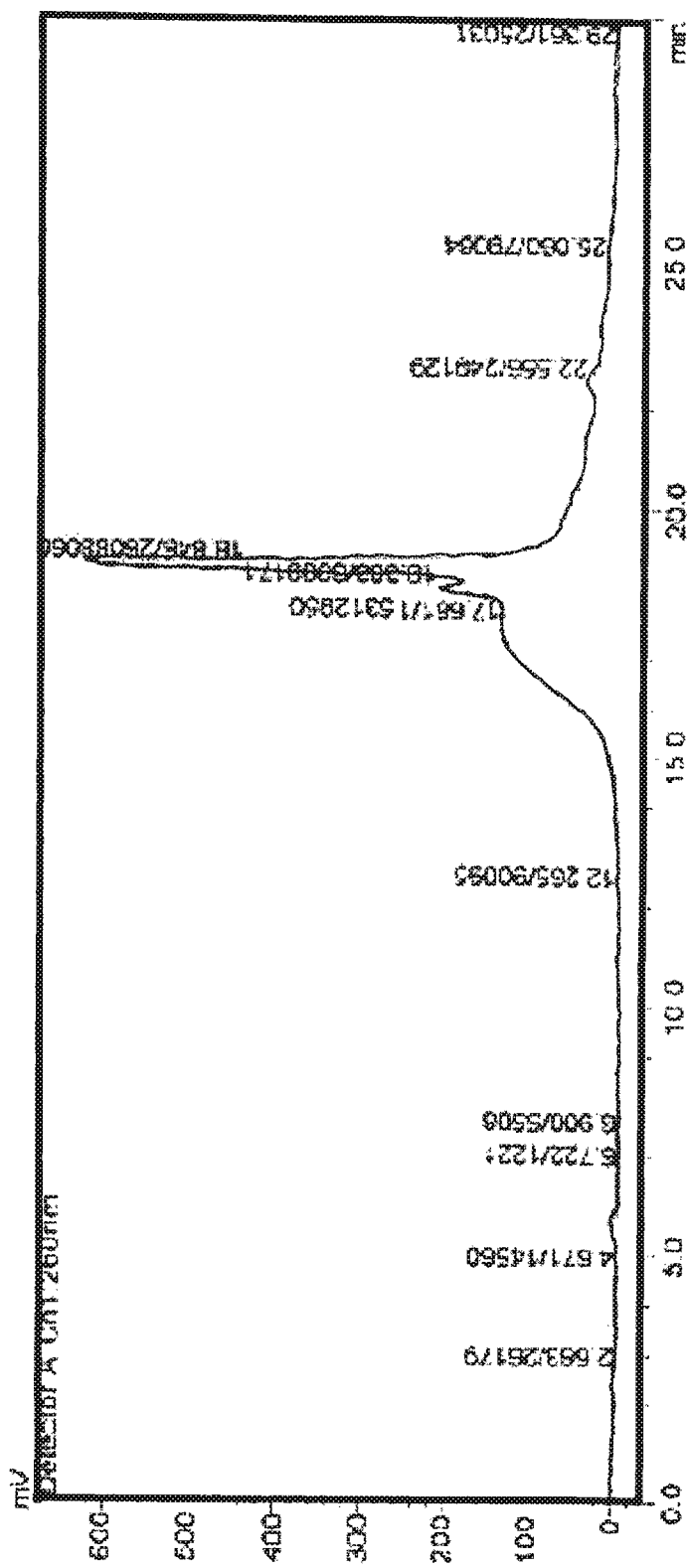
FIG. 9 shows an HPLC ultraviolet spectrum of the wolfberry glycopeptide composition of the present invention as prepared in Example 5.
Figure 10:
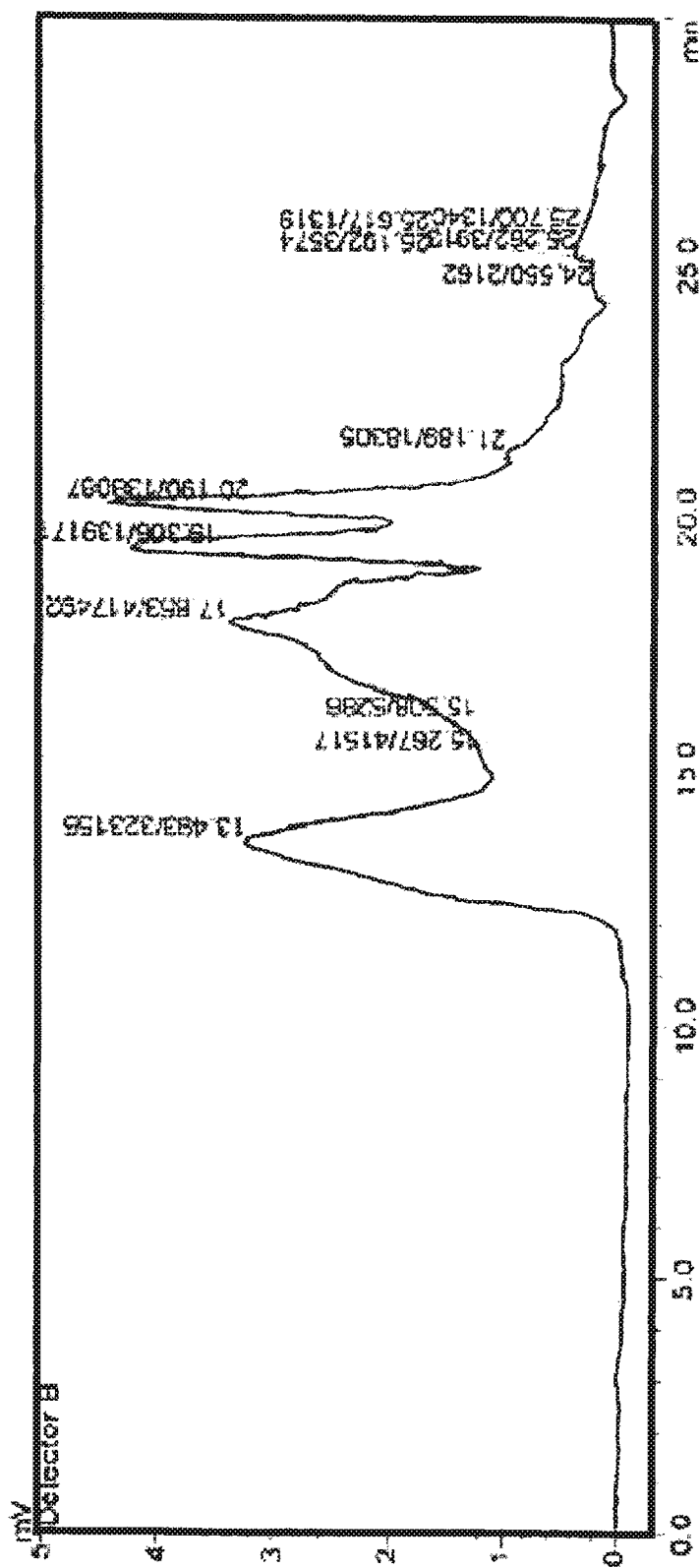
FIG. 10 shows an HPLC differential refractive index map of the wolfberry glycopeptide composition of the present invention as prepared in Example 5.

The wolfberry glycopeptide is analyzed by HPLC and determined to have the part with a molecular weight of 1000-10000 Da accounting for 65%; the protein content is at 30% weight percentage as determined by Kjeldahl method, the neutral polysaccharide content is at 25% weight percentage as determined by anthrone-sulfuric acid method, and uronic acid content is at 15% weight percentage as determined by carbazole method. FIG. 9 shows the HPLC ultraviolet spectrum, and FIG. 10 shows the HPLC differential refractive index map of the wolfberry glycopeptide.

Example 6. Preparing Glycopeptide Composition of the Present Invention with Fresh Fruits Fresh fruit of wolfberry 400 g is smashed and soaked in deionized water. The amount of the deionized water is at a mass ratio of 5 times to that of the fresh fruits, and soaking is conducted at 35° C. for 2 hours. The soaking liquid is centrifuged at 3000 rpm in a CR22G centrifuge for 1 minute to obtain a supernatant that is still turbid.

The supernatant is placed in a water bath and heated to 70° C. for 0.5 hours. The pulp and pectin remained in the supernatant congregate to a flocculation. The liquid is placed in a CR22G centrifuge and centrifuged at 13,000 rpm for 10 seconds to obtain a clear solution with a light transmittance of 90%.

The clear solution is placed in an ultrafiltration device for ultrafiltration. The molecular weight cutoff of the ultrafiltration membrane is 1000 Da, and the working pressure is 5 kg. Deionized water is continuously supplemented to the cut-off solution. When the conductivity of the cut-off solution is decreased to 900 us/cm and the sugar degree to 1.2, the solution containing macromolecular portion cut-off is collected, concentrated, and freeze-dried to obtain 1.05 g wolfberry glycopeptide.

Figure 11:
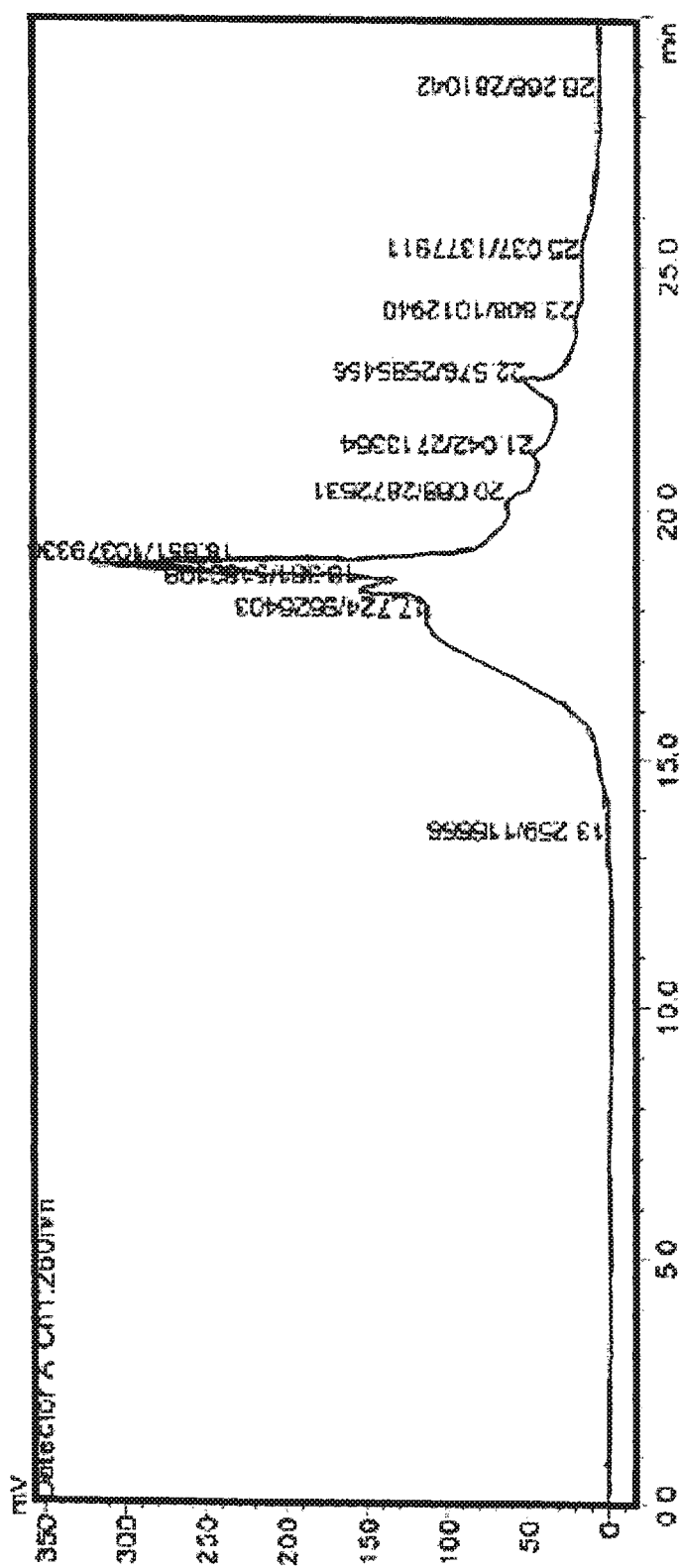
FIG. 11 shows an HPLC ultraviolet spectrum of the wolfberry glycopeptide composition of the present invention as prepared in Example 6.
Figure 12:
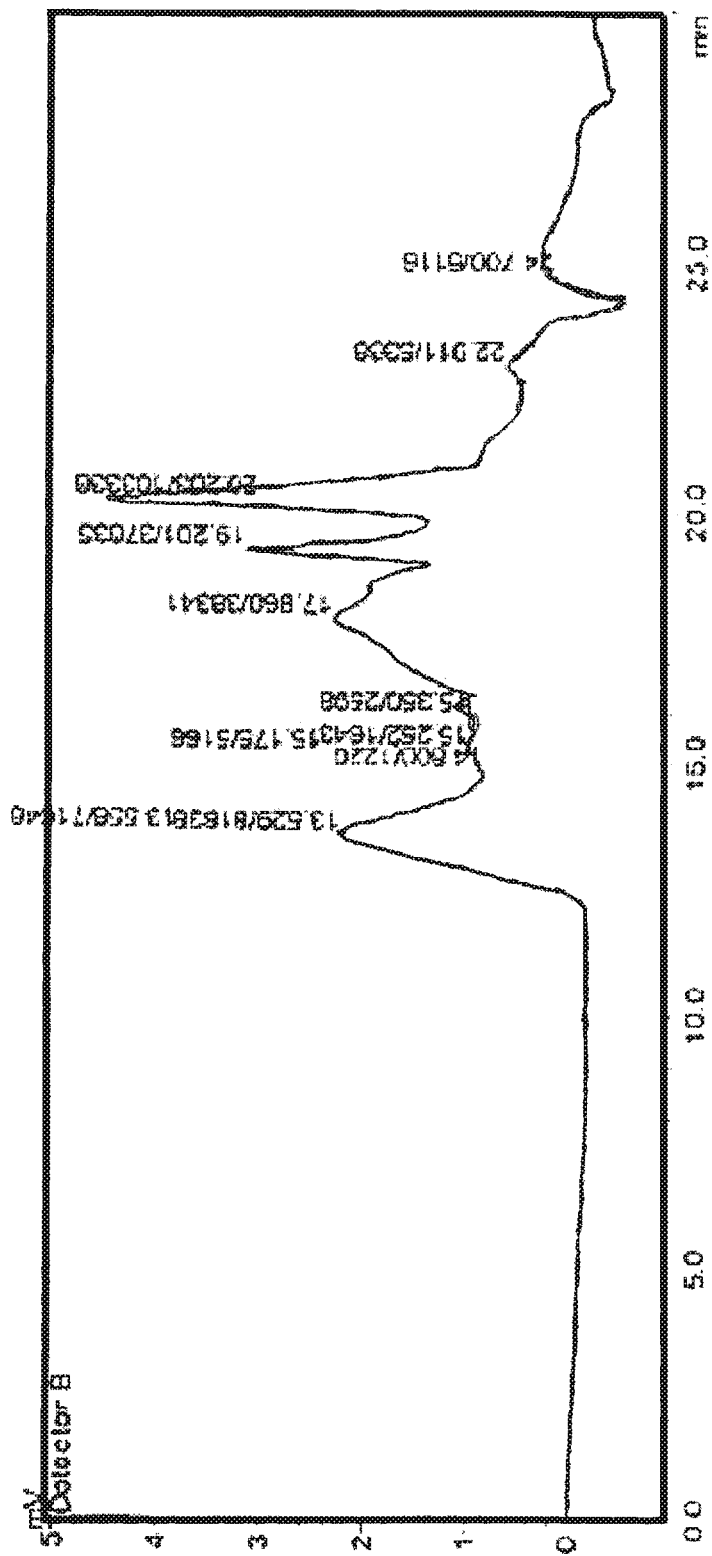
FIG. 12 shows an HPLC differential refractive index map of the wolfberry glycopeptide composition of the present invention as prepared in Example 6.

The wolfberry glycopeptide is determined by HPLC to have the part with a molecular weight of 1000-10000 Da accounting for 55%; the protein content is at 25% as determined by Kjeldahl method, the neutral polysaccharide content is at 30% as determined by anthrone-sulfuric acid method, and the uronic acid content is at 15% as determined by carbazole method. FIG. 11 shows the HPLC ultraviolet spectrum and FIG. 12 shows the HPLC differential refractive index map of the wolfberry glycopeptide.

Comparative Example 1. Preparing Wolfberry Polysaccharide by Conventional Process Dried fruit of wolfberry 50 g is smashed, then soaked in a deionized water at a mass ratio of 10 times to the amount of dried fruits. Soaking is conducted at 25° C. for 4 hours. The soaking liquid is placed in a CR22G centrifuge and centrifuged at 1000 rpm for 1 minute to obtain a supernatant that is still turbid.

The supernatant is concentrated to 75 g by heating, and 450 mL of absolute ethanol is added to the supernatant, followed by stirring to obtain a brown precipitate. The mixture is centrifuged to get the precipitate, and the precipitate is dried at 100° C. to obtain 5.0 g wolfberry polysaccharide.

Figure 13:
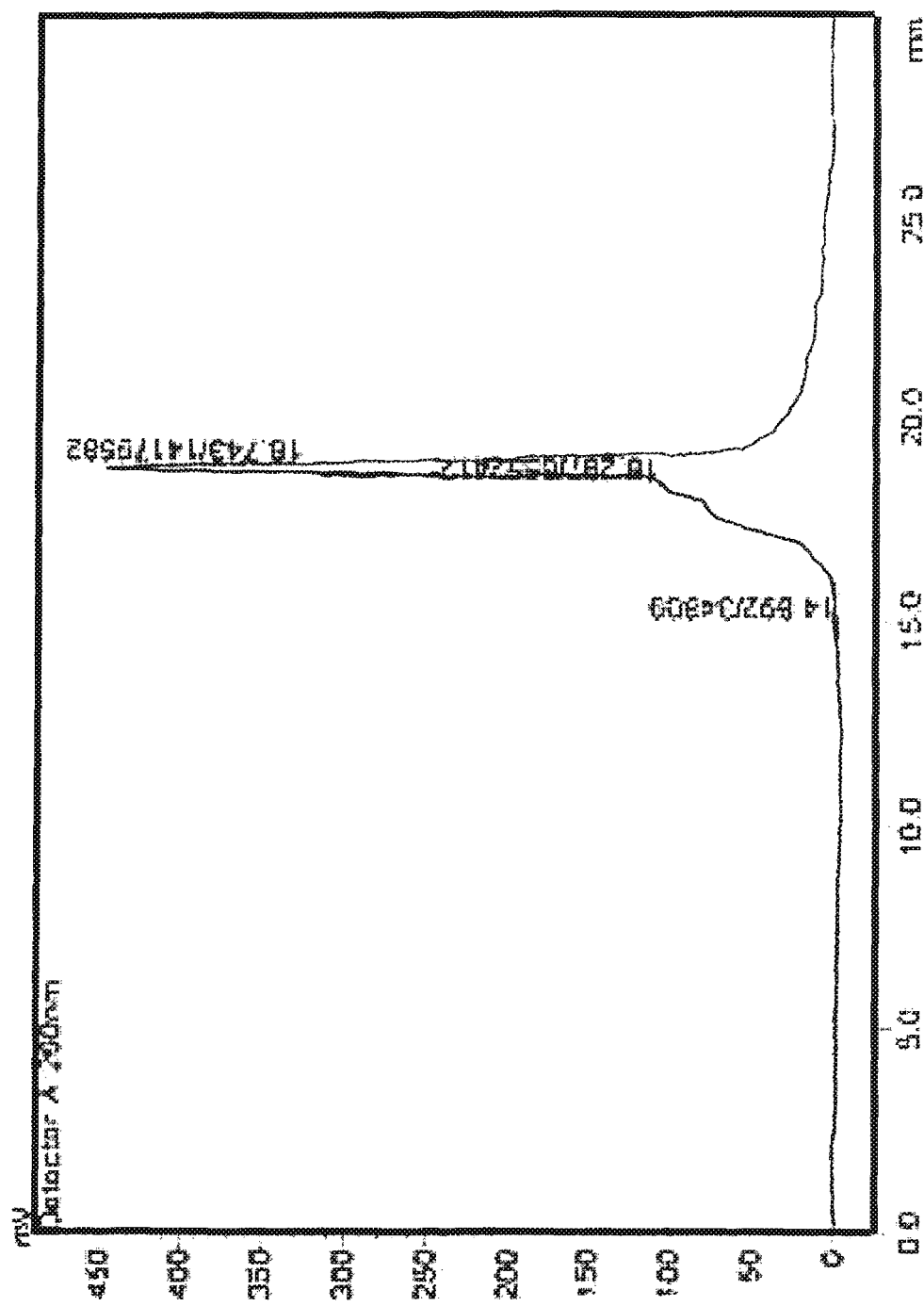
FIG. 13 shows an HPLC ultraviolet spectrum of the wolfberry polysaccharide as prepared in Comparative Example 1.
Figure 14:
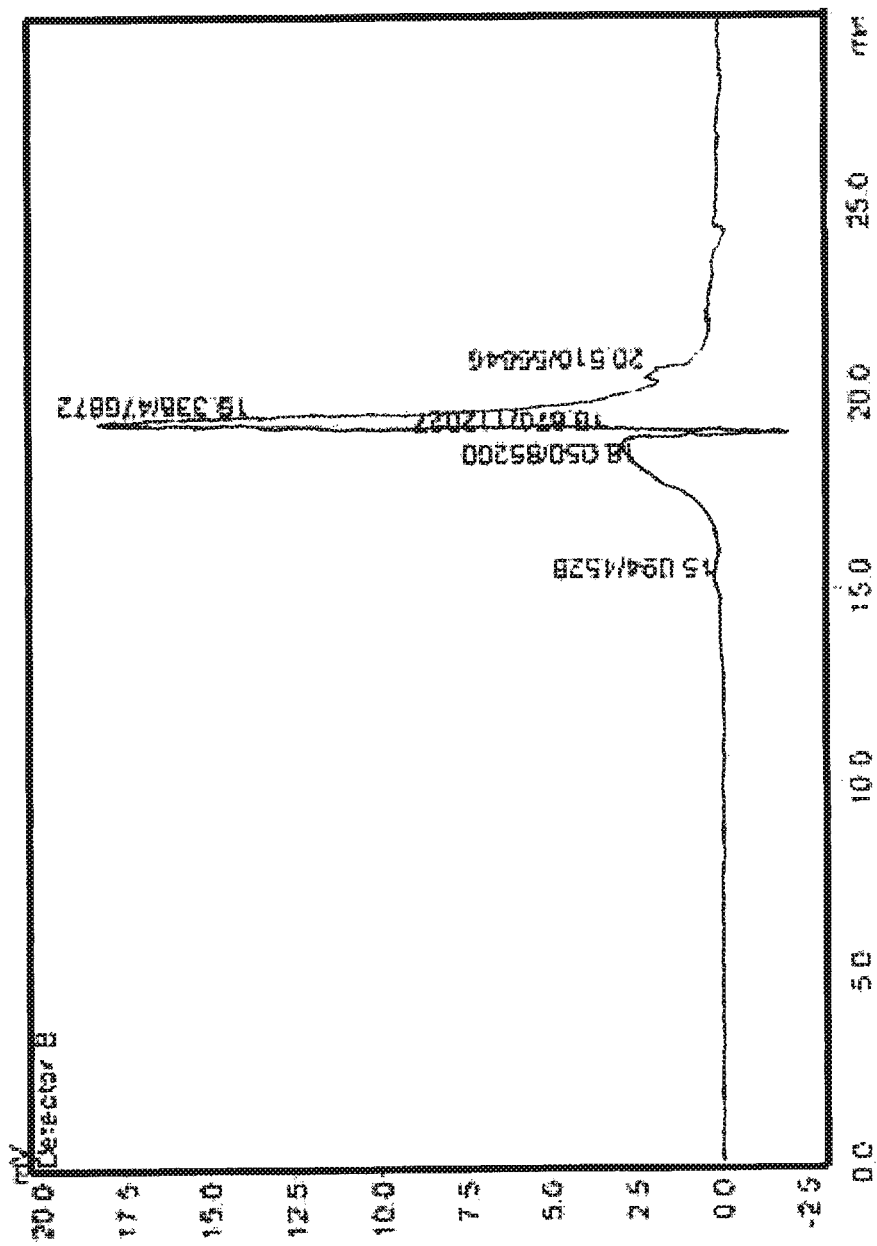
FIG. 14 shows an HPLC differential refractive index map of the wolfberry polysaccharide as prepared in Comparative Example 1.

The wolfberry polysaccharide is determined by HPLC to have the part with a molecular weight of 1000-10000 Da accounting for 30%, the protein content is 6.5% as determined by Kjeldahl method, the neutral polysaccharide content is 35% as determined by anthrone-sulfuric acid method, and uronic acid content is 7% as determined by carbazole method. FIG. 13 shows the HPLC ultraviolet spectrum, and FIG. 14 shows the HPLC differential refractive index map of the wolfberry glycopeptide.

Comparing with the products of the present invention in Examples 1 to 6, the product by the method using organic solvent extraction yields far less macromolecular contents and far less protein and uronic acids, while the contents of polysaccharide slightly increases or remains the same.

Example 7. Effect on Proliferation of Mouse Spleen T Lymphocytes

Experimental mice are divided into a control group and three wolfberry glycopeptide experimental groups of different doses, with 10 mice per group. T lymphocyte mitogen ConA is added to mouse hepatocytes and assayed by $^3$H-thymidine ($^3$H-TdR) incorporation method. The mice of the wolfberry glycopeptide experimental groups are injected with the wolfberry glycopeptide of Example 1 at doses of 1.0, 2.0, and 5.0 mg/Kg·d for 7 consecutive days. Then, their spleens are taken and the content of $^3$H-TdR in the spleens is measured. Results are shown in Table 1.

TABLE 1

Experimental results on T lymphocyte proliferation

| Groups | Dosage (mg/Kg · d) | $^3$H-TdR incorp cmp × $10^{-2}$ | percentage increased |
|---|---|---|---|
| Control | NS | 285 ± 23 | 0 |
| Wolfberry Glycopeptide | 1.0 | 463 ± 42** | 63%** |
| Wolfberry Glycopeptide | 2.0 | 658 ± 28*** | 131%*** |
| Wolfberry Glycopeptide | 5.0 | 495 ± 40** | 74%** |

$P < 0.01$ $P < 0.001$ Compared with that in the control group

As shown in Table 1, in the mice injected with wolfberry glycopeptide at doses of 1.0, 2.0, and 5.0 mg/Kg-d, after 7 days, the proliferation of mouse spleen T lymphocytes induced by ConA has increased by 63%, 131%, and 74% compared with that in the control group. Thus, the injection of wolfberry glycopeptide of the present invention significantly enhances the proliferation of mouse spleen T lymphocytes induced by ConA.

Example 8. Effect on Proliferation of Mouse Spleen T Lymphocytes

Experimental mice are divided into a control group and two wolfberry glycopeptide experimental groups of different doses, with 8 mice per group. T lymphocyte mitogen ConA is added to mouse hepatocytes and assayed by $^3$H-thymidine ($^3$H-TdR) incorporation method. The wolfberry glycopeptide of Example 1 is orally administered at doses of 5 or 10 mg/Kg·d for 7 days, and the proliferation of mouse spleen lymphocytes measured on the 7th day is shown in Table 2.

TABLE 2

Results on spleen lymphocyte proliferation

| Group | dose mg/Kg · d | $^3$H-TdR incorporation (cmp) | | Multiple increased | Percentage increased |
|---|---|---|---|---|---|
| | | No ConA induction | ConA induction | | |
| Control | NS | 450 ± 241 | 28140 ± 3110 | 62.5 | 0 |
| Glycopeptide | 5 | 461 ± 273 | 64870 ± 2571 ** | 140.7 | 125% ** |
| Glycopeptide | 10 | 413 ± 170 | 37354 ± 2606 ** | 90.4 | 45% ** |

** $P < 0.01$ Compared with that in the control group

As shown in Table 2, in the mice injected with wolfberry glycopeptide at doses of 5 and 10 mg/Kg-d, after 7 days, the proliferation of mouse spleen T lymphocytes induced by ConA has increased by 125% and 45% compared with that in the control group. Thus, oral administration of the wolfberry glycopeptide composition of the present invention significantly enhances the proliferation of mouse spleen T lymphocytes induced by ConA.

Example 9. Effects on Proliferation of T and B Lymphocytes

Normal Balb/c mice are randomized into groups, 10 mice for each group. Each mouse in the sample intervention group is intragastric administered with 0.2 ml test sample per day, and the samples included the wolfberry glycopeptides prepared in Examples 2, 4, 6 and wolfberry polysaccharide obtained in Comparative Example 1. The administration period is 9 days. Normal control group is administered with the same volume of a solvent in same manner without any wolfberry extract, and is continuously intervened for 9 days. The wolfberry crude extract used in the crude extract group is prepared by grinding dry fruit of wolfberry with pure water to a concentration of 200 mg/kg, and each mouse is intragastric administered with 0.2 ml of the crude extract per day.

The proliferation ability of T and B lymphocytes is tested as follow: the cell concentration of each cell sample is adjusted to $4 \times 10^6$/ml. 100 μl of cell suspension and 100 μl of mitogen (ConA or LPS) are added to each well of a 96-well plate for a total volume of 200 μl. Another control cell sample without mitogen is used as a background control for cell proliferation. The cells are cultured for 48 hours in a 37° C. incubator containing 5% $CO_2$, and 20 μl of $^3$H-thymidine nucleotide is added to each well 12 hours before the end of the culture. At the time of measurement, the labeled cell samples are collected to a glass fiber membrane by a cell harvester. After adding scintillation fluid, the amount of $^3$H-thymidine nucleotide incorporated into the cell DNA is read on a Beta counter. The cell proliferation is represented by cpm value. The test results of T lymphocyte proliferation levels are shown in Table 3:

TABLE 3

Test results on T lymphocyte proliferation

| Group | dose (mg/kg) | T lymphocyte proliferation level (cpm value) | Percentage increased |
|---|---|---|---|
| Normal control | / | 894 ± 42 | 0 |
| Glycopeptide in Example 2 | 2 | 1373 ± 80 *** | 54% *** |
| Glycopeptide in Example 4 | 2 | 1287 ± 36 *** | 43% *** |
| Glycopeptide in Example 6 | 2 | 1248 ± 65 *** | 40% *** |
| Polysaccharide in comparative Example 1 | 2 | 992 ± 76 | 0.1% |
| Crude extract | 200 | 1189 ± 123 * | 33% * |

* $p < 0.05$, *** $p < 0.001$ Compared with that in the normal group

As shown in Table 3, the wolfberry glycopeptide prepared in Examples 2, 4, and 6 show increased proliferation of T lymphocytes by 54%, 43%, and 40%, respectively, compared with that in the control group. The polysaccharide of Comparative Example 1 only shows increase in the proliferation of T lymphocytes by 0.1% compared with the that in the control group, and no significant improvement is observed. The wolfberry crude extract group shows improvement of 33% over the control group, but its improved effect is not as high as the wolfberry glycopeptide composition of the present invention.

The test results of B lymphocyte proliferation level are shown in Table 4:

TABLE 4

Test results on B lymphocyte proliferation

| Group | dose (mg/kg) | B lymphocyte proliferation level (cpm value) | Percentage increased |
|---|---|---|---|
| Normal control | / | 2103 ± 110 | 0 |
| Glycopeptide in Example 2 | 2 | 3041 ± 183 *** | 45% *** |
| Glycopeptide in Example 4 | 2 | 2842 ± 150 *** | 35% *** |
| Glycopeptide in Example 6 | 2 | 2694 ± 139 *** | 28% *** |
| Polysaccharide in Comparative Example 1 | 2 | 2327 ± 168 | 11% |
| Crude extract | 200 | 2641 ± 245 | 26% |

* $p < 0.05$, *** $p < 0.001$ Compared with that in the normal group

As shown in Table 4, the wolfberry glycopeptide prepared in Examples 2, 4, and 6 show increased proliferation of B lymphocytes by 45%, 35%, and 28%, respectively, compared with that in the control group. Wolfberry polysaccharide of Comparative Example 1 only shows increased proliferation of B lymphocytes by 11% compared with that in the control group. The wolfberry crude extract group shows improvement of 26% over the control group, but its improvement is not as high as the wolfberry glycopeptide composition of the present invention.

Test results show that oral administration of the wolfberry glycopeptide composition of the present invention on normal Balb/c mice for 9 days significantly increase the proliferation ability of T and B lymphocytes. The same dose of wolfberry polysaccharide has no obvious or only slight effect on the immune proliferation ability. Compared with the relatively equal amount of the wolfberry crude extract, the wolfberry glycopeptide composition of the present invention is better in promoting the proliferation ability of the immune cells.

Example 10. Effect on Regulating Proliferation of T and B Lymphocytes

Balb/c mice are randomized into 7 groups, with 10 mice for each group. Normal control group is administrated with an equal volume of saline solution; the wolfberry glycopeptide groups are administrated with different doses of the wolfberry glycopeptide prepared in Example 1 as shown in Table 5; and the wolfberry crude extract group is administered according to the concentrations as shown in Table 5; the model control group is intraperitoneally injected with 75 mg/kg (0.1 mL/10 g) of cyclophosphamide (CTX).

All the groups are administered one week earlier, except for the normal control group (an equal volume of normal saline solution is administered), the other groups are intraperitoneal injected with 75 mg/kg CTX on the 1st, 4th, and 7th day of the experiment.

After the first CTX attack, the administration is continued for 9 days. The normal control and the model control groups are administered with same volume of normal saline in the same manner. Mice are sacrificed on the 10th day and examined for results.

(1) Indicator 1: Spleen Index

The spleen is an important immune organ, and the spleen index reflects the strength of the body's immune function to certain extent. The level of the spleen index depends on the degree of lymphocyte proliferation, and based on the level of the spleen index, one can roughly estimate the strength of the immune function. The test results of the effect of wolfberry glycopeptides of the present invention on the spleen index of mice injected with CTX are shown in Table 5:

TABLE 5

Test result on the spleen index of mice injected with cyclophosphamide

| Groups | dose(mg/kg) | Spleen index (mg/g) | Percent change |
|---|---|---|---|
| Normal control | / | 4.07 ± 0.18 | 0 |
| Model control | 2 | 1.59 ± 0.07 | −61% ### |
| Glycopeptide | 3.75 | 2.30 ± 0.22 | +45% ** |
| Glycopeptide | 7.5 | 2.01 ± 0.02 *** | +26% *** |
| Glycopeptide | 15 | 2.60 ± 0.20 | +64% *** |
| Glycopeptide | 30 | 3.20 ± 0.30 *** | +101% *** |
| Crude extract | 200 | 2.00 ± 0.20 | +26% |

$p < 0.001$ compared with normal group;
 $p < 0.01$, * $p < 0.001$ compared with model group As shown in Table 5, in the model control group, CTX significantly reduces the spleen index of the experimental mice with a reduction degree of 61%. The group using the wolfberry glycopeptides prepared by the present invention significantly increase the spleen index of CTX-attacked experimental mice by 26% to 101% from the model control group, and show concentration-dependent relationship. The wolfberry crude extract shows an increase in the spleen index by 26%.

(2) Indicator 2: Total Number of Spleen Cells

The total number of spleen cells is the sum of the free suspending cells released by the spleen after removal of red blood cells, and it mainly includes the number of T and B lymphocytes, antigen-presenting cells (such as macrophages and dendritic cells), and other immune cells. The number reflects the strength of the immune function to a certain extent. The test results of the effect of the wolfberry glycopeptide composition of the present invention on the total number of spleen cells in mice injected with CTX are shown in Table 6:

TABLE 6

Test results on spleen cells in CTX-attacked experimental mice.

| Group | dose (mg/kg) | Total no of spleen cells (×10$^7$) | Percent change |
|---|---|---|---|
| Normal control | / | 8.49 ± 0.19 | 0 |
| Model control | 2 | 3.60 ± 0.24 ### | −58% ### |
| Glycopeptide | 3.75 | 4.20 ± 0.14 | +17% |
| Glycopeptide | 7.5 | 4.21 ± 0.09 * | +17% * |
| Glycopeptide | 15 | 5.00 ± 0.18 *** | +39% *** |
| Glycopeptide | 30 | 6.25 ± 0.20 *** | +74% *** |
| Crude extract | 200 | 4.30 ± 0.22 * | +19% * |

$p < 0.001$ compared with normal group;
*$p < 0.05$, ***$p < 0.001$ compared with model group As shown in Table 6, in the model control group, CTX significantly reduces the total number of spleen cells in the experimental mice with a reduction rate of 58%. The group using the wolfberry glycopeptide composition of the present invention at a higher concentration significantly increase the total number of spleen cells in CTX attacked experimental mice, and the maximum increase is 74% from the model control group, and which had a concentration-dependent relationship and statistics difference. Finally, wolfberry crude extract also increases the total number of spleen cells by 19% with statistical difference.

(3) T Lymphocyte Proliferation

The detection of the ability of lymphocyte proliferation is the most important index for evaluating immune function. Mitogen ConA mainly induces T lymphocyte proliferation. The testing procedure is described in Example 9, using ConA at a concentration of 2 μg/mL. The test results of the effect of wolfberry glycopeptide composition of the present invention on the proliferation of T lymphocyte in mice injected with CTX are shown in Table 7:

TABLE 7

Effect on T lymphocyte proliferation of CTX attacked mice

| Group | dose (mg/kg) | T lymphocyte proliferation level (cpm value) | Percent change |
|---|---|---|---|
| Normal control | / | 13098 ± 854 | 0 |
| Model control | / | 1797 ± 213### | −86%### |
| Glycopeptide | 3.75 | 1773 ± 124 | −1% |
| Glycopeptide | 7.5 | 1670 ± 137 | −7% |
| Glycopeptide | 15 | 1773 ± 95 | −1% |
| Glycopeptide | 30 | 2347 ± 41 * | +31% * |
| Crude extract | 200 | 1937 ± 149 | +8% |

$p < 0.001$ compared with normal group;
* $p < 0.05$ compared with model group As shown in Table 7, under the condition of ConA (2 μg/mL), the model control group shows that CTX significantly reduces the proliferation level of T lymphocytes in experimental mice (normal control compared with model control, $p<0.001$ ###), with a reduction rate of 86%. Higher concentration of the wolfberry glycopeptide (30 mg/kg) of the present invention and wolfberry crude extract promote the T lymphocyte proliferation in CTX attacked mice with statistical significance ($p<0.05$*).

(4) B Lymphocyte Proliferation

Mitogen LPS mainly induces B lymphocyte proliferation. The test procedure is described in Example 9, using LPS at a concentration of 2 μg/mL. The test results of the effect of wolfberry glycopeptide composition of the present invention on the proliferation of B lymphocyte in mice injected with CTX are shown in Table 8:

TABLE 8

Test results on B lymphocyte proliferation in CTX attacked mice

| Group | dose (mg/kg) | B lymphocyte proliferation level (cpm value) | Percentage change |
|---|---|---|---|
| Normal control | / | 12726 ± 440 | 0 |
| Model control | / | 1413 ± 84 ### | −89% ### |
| Glycopeptide | 3.75 | 1221 ± 34 | −14% |
| Glycopeptide | 7.5 | 1325 ± 92 | −6% |
| Glycopeptide | 15 | 1495 ± 121 | +6% |
| Glycopeptide | 30 | 1869 ± 106 *** | +32% *** |
| crude extract | 200 | 1679 ± 129 | +19% |

$p < 0.001$ compared with normal group;
* $p < 0.001$ compared with model group As shown in Table 8, under the condition of low concentration of LPS (2 μg/mL), the model control group shows that CTX significantly reduces the proliferation level of B lymphocytes in the experimental mice with a reduction rate of 89%. The group using the wolfberry glycopeptide composition of the present invention and the wolfberry crude extract show a trend of promoting the proliferation of B lymphocytes in CTX-attacked experimental mice, and exhibit a dose-effect relationship to some extent, but only high doses of glycopeptide (30 mg/kg) shows statistical difference ($p<0.001$*).

In conclusion, the experimental results show that the wolfberry glycopeptide composition of the present invention has a good immune protective effect on the immuno-compromised mouse model induced by CTX. The wolfberry glycopeptide composition of the present invention restores the total amount of immune cells, as shown by the increase in the spleen index and total number of spleen cells, in a concentration-dependent manner during CTX attack process, and improves the proliferation ability of immune cell, as shown by ConA and LPS-induced immune cell proliferation, to some extent. Due to the severe damage of CTX on the overall immune system, the immune cells are drastically reduced and the function of cellular reaction is low. The wolfberry glycopeptide of each concentration shows a trend of protecting immune system under overall conditions, but only high-dose of immune glycopeptide has a clear protective effect on the ability of immune cell proliferation.

Example 11. Effect on the Activity of Mouse NK Cells

Natural Killer cells (NK cells) are important immune cells in the body, which is not only related to anti-tumor, anti-viral infection, and immune regulation, but also involved in the hypersensitivity and occurrence of autoimmune diseases in some cases. NK cells identify target cells and killing medium. Experimental Kunming mice are divided into 3 groups with 8 mice in each group. The wolfberry glycopeptide of Example 1 is administered orally at a dose of 5 or 10 mg/Kg-d in the wolfberry glycopeptide group. An equal volume of normal saline is administered for 3 days in the control group. The cytotoxicity function of mouse NK cells is determined on the 3rd day. The mice are dissected the next day after the last administration, and the spleen is aseptically taken to prepare cell suspension, from which red blood cells are removed, MTT staining is performed, and OD value is measured to calculate the cytotoxicity function, i.e., the killing rate, of the NK cells. The test results are shown in Table 9.

TABLE 9

Test results on NK cell activity

| Groups | Dose (mg/kg) | Killing rate (%) |
|---|---|---|
| Control | / | 12.4 |
| Wolfberry Glycopeptide | 5 mg/Kg | 17.7** |
| Wolfberry Glycopeptide | 10 mg/Kg | 9.5 |

**p < 0.01 compared with control group

As shown in FIG. 9, oral administration of 5 mg/Kg wolfberry glycopeptide in mice significantly improves the killing rate, i.e., the immune activity of NK cells.

Example 12. Effect on the Activity of NK Cells in $S_{180}$ Tumor-Bearing Mice

Experimental Kunming mice are divided into 5 groups with 8 mice in each group. The control group is directly administered with an equal volume of normal saline; $S_{180}$ sarcoma is inoculated on the toe in the mice of the $S_{180}$ tumor-bearing group; $S_{180}$ sarcoma is inoculated on the toe and the wolfberry glycopeptide of Example 1 is intraperitoneally injected at doses of 1-5 mg/Kg for a period of 7 days in the wolfberry glycopeptide groups. The activity of NK cells is measured in the same manner as in Example 11. The results are shown in Table 10.

TABLE 10

Test results (injection) on NK cell activity

| Group | Dose (mg/Kg · d) | Activity of NK cells (%) |
|---|---|---|
| Control | / | 41.3 ± 1.3 |
| $S_{180}$ tumor-bearing group | / | 21.3 ± 4.2** |
| $S_{180}$ + wolfberry glycopeptide | 1.0 | 47.5 ± 1.5*+++ |
| $S_{180}$ + wolfberry glycopeptide | 2.0 | 59.1 ± 1.1***+++ |
| $S_{180}$ + wolfberry glycopeptide | 5.0 | 43.2 ± 1.4+++ |

*p < 0.05 p < 0.01 *p < 0.001 Compared with that in the control group
+++p < 0.001 Compared with that in the $S_{180}$ tumor-bearing group As shown in Table 10, the immune activity of the NK cells in the $S_{180}$ tumor-bearing mice is significantly lower than that in the normal mice. As for the immuno-compromised mouse model caused by $S_{180}$ sarcoma bearing, the wolfberry glycopeptide composition of the present invention significantly improves the killing rate of NK cells, suggesting that it has good immune protective effect on the tumor-bearing mice.

Example 13. Glycopeptide Promotes IL-2 Proliferation in Mouse Thymocytes In Vitro The spleens of C57BL/6 mice are aseptically taken, and the spleen cells are isolated to prepare a spleen cell suspension. ConA is added for culturing, and the culture solution is centrifuged and filtered to obtain a IL-2 test sample. The wolfberry glycopeptide of Example 1 is added to culture solution of IL-2 at a concentration of 0-500 μg/ml; IL-2 activity is determined by the incorporation of $^3$H-Tdr (cmp) in thymocytes in vitro. Three groups of parallel test are performed. The test results are shown in Table 11:

TABLE 11

Cell experimental results on IL-2 production

| Wolfberry Glycopeptide (μg/ml) | Incorporation of $^3$H-Tdr (cmp) | | |
|---|---|---|---|
| | 1 | 2 | 3 |
| 0 | 888 ± 14 | 490 ± 116 | 738 ± 105 |
| 10 | 1607 ± 55** | 1571 ± 346** | 1781 ± 414** |
| 50 | 2181 ± 139** | 1509 ± 72** | 2410 ± 116** |
| 250 | 2690 ± 365** | 1845 ± 366** | 2415 ± 115** |
| 500 | 805 ± 21 | 821 ± 208* | 1088 ± 370 |

*p < 0.05 **p < 0.01 Compared with control group

As shown in Table 11, the prepared IL-2-containing supernatant increased the proliferative activity of adult mouse thymocytes in vitro, indicating that the wolfberry glycopeptide had an enhanced effect on IL-2 activity.

Example 14. Wolfberry Glycopeptide Promotes IL-2 Production in Mouse Spleen Cells C57BL/6 mice are selected and divided into groups with 8 mice in each group. An equal volume of normal saline is administrated by subcutaneous injection in the mice of the control group; the wolfberry glycopeptide of Example 1 is administrated by subcutaneous injection at a concentration of 2 mg/Kg for 7 days in the wolfberry glycopeptide group. The mouse spleen cells are taken on the 8th day, and IL-2 activity is determined by the incorporation of $^3$H-Tdr (cmp) in thymocytes in vitro. The results are shown in Table 12.

TABLE 12

Test results (injection) on IL-2 production

| Groups | Dose (mg/Kg · d) | IL-2 activity (cmp) |
|---|---|---|
| Control | / | 1550 ± 101 |
| Wolfberry Glycopeptide | 2.0 | 2807 ± 226** |

**p < 0.01 Compared with that in the control group

As shown in Table 12, the wolfberry glycopeptide significantly increases the production of IL-2 in spleen cells by 81% compared with that in the control group.

Example 15. Effect on Specific Killing Effect in Immunized Mice

CT57BL mice are divided into 4 groups with 8 mice in each group. The mice are subcutaneously injected with 5×10$^6$ P815 cells sub-cultured for 48 hours to be initially sensitized, and the control group is injected with normal saline solution instead. After 3 days, the drug-administered group is continuously administered by intraperitoneal injection. The control group and the immunized control group are injected with normal saline solution, while levamisole (LMS) is orally administered at a dose of 0.38 mg/Kg·d for 3 days in the immunized mice+LMS group, and the specific killing rate is determined on the 12th day; the wolfberry glycopeptide of Example 1 is orally administered at a dose of 5 mg/Kg·d for 7 days in the immunized mice+wolfberry glycopeptide group, and the specific killing rate is determined on the 15th day. The mice are sacrificed and the spleen cells are taken to determine the specific killing activity of CTL on P815 target cells. The target cells are pre-labeled with ³HTdR. The percentage of killing is calculated according to the method disclosed at Wang Baikun, "Immunological pharmacological action of wolfberry polysaccharide on T, killing T and NK cells and the counteraction of immunosuppressive action on cyclophosphamide," Chinese Journal of Pharmacology and Toxicology, No. 4, pp. 39-43 (1990), the content of which is incorporated herein by reference. The test results are shown in Table 13.

TABLE 13

Test results on specific killing rate in immunized mice

| Groups | Supernatant (cmp) | Specific killing rate (%) |
|---|---|---|
| Control | 196 ± 17 | — |
| Immunized mice | 608 ± 138 | 33.1 |
| Immunized mice + LMS | 789 ± 178* | 48.4* |
| Immunized mice + glycopeptide | 1029 ± 47** | 67.0** |

*$p < 0.05$ **$p < 0.01$ Compared with that in the control group

As shown in Table 13, the wolfberry glycopeptide increases the specific killing rate of the immunized mice.

Example 16. Effect on Specific Killing Rate of Mice Immunized with Cyclophosphamide Experimental mice are divided into groups with 8 mice in each group. A single dose of 5 mg/Kg CTX is injected, and the result is determined on the 6th day. Wolfberry glycopeptide of Example 1 is orally administered at 5-10 mg/Kg·d for 6 days. The specific killing rate is measured on the 12th day. The detection method is the same as in Example 15 and the results are shown in Table 14.

TABLE 14

Test results on specific killing rate of immunized mice injected with CTX

| Group | Supernatant (cmp) | Specific killing rate(%) | Inhibition ratio (%) |
|---|---|---|---|
| Immunized mice | 892 ± 39 | 70.0 | — |
| Immunized mice + CTX | 598 ± 32 | 34.0 | 51.4 |
| Immunized mice + CTX + 5 mg/Kg glycopeptide | 786 ± 33** | 56.7 | 19.0 |
| Immunized mice + CTX + 10 mg/Kg glycopeptide | 681 ± 11** | 44.6 | 36.3 |

**$p < 0.01$ Compared with that in the control group

As shown in Table 14, the wolfberry glycopeptide antagonizes the inhibitory effect of CTX on the specific killing rate of immunized mice.

Example 17. Anti-Lipid Peroxidation of Wolfberry Glycopeptides

40 SD rats are randomly divided into normal control group, $CCl_4$ model group, and wolfberry glycopeptide groups at low, medium, and high dose (1, 5, and 10 mg/kg), with 8 rats in each group. Wolfberry glycopeptide prepared in Example 1 is subcutaneously injected once a day for 7 continuous days in the wolfberry glycopeptide group. After the last administration, the mice are fasted for 16 hours, PO 0.2% $CCl_4$ 2 mL/Kg, and sacrificed after 30 minutes to prepare the liver mitochondrial suspension. The solution is mixed with 0.15 mol/L KCl and 0.15 mol/L phosphate buffer, and the reaction is terminated immediately after incubation at 37° C. for 30 minutes. The mixture is centrifuged at 3000 rpm for 10 minutes. 1 mL supernatant is taken, and 1 mL 0.67% thiobarbituric acid is added. The solution is heated at 100° C. for 10 minutes to develop color. After cooling, OD values at 535 nm and 520 nm ($OD_{535\ nm-520\ nm}$) are measured, respectively. The difference is linear with the lipid peroxide content. The test results are shown in Table 15:

TABLE 15

Results in anti lipid peroxidation test

| Groups | ($OD_{535\ nm-520\ nm}$) |
|---|---|
| Control group | 0.25 ± 0.04 |
| $CCl_4$ | 0.47 ± 0.07*** |
| $CCl_4$ + 1 mg/Kg glycopeptide | 0.37 ± 0.04 |
| $CCl_4$ + 5 mg/Kg glycopeptide | 0.19 ± 0.06+++ |
| $CCl_4$ + 10 mg/Kg glycopeptide | 0.25 ± 0.05++ |

***$p < 0001$ compared with control group;
++$p < 0.01$ +++$p < 0.001$ compared with $CCl_4$ group As shown in Table 15, the lipid peroxide of the group administrated with wolfberry glycopeptide composition of the present invention is significantly decreased than that in the $CCl_4$ group, suggesting that the glycopeptides protect the liver cells from lipid peroxidation damage caused by free radicals at a dose of 5-10 mg/Kg.

Example 18. Effect on Spleen Weight and Cerebral Cortex in Mice Under Physical Stress Effects of wolfberry glycopeptide composition of the present invention on the weight of spleen and cerebral cortex in mice under physical stress after electroshock (ES) and γ-ray (R) irradiation are examined. Experimental mice are divided into 4 groups with 10 mice in each group as shown in Table 16. No administration for the normal control group. An equal volume of normal saline is administered in the ES+R (saline) group. The wolfberry glycopeptide of Example 1 is administered in doses of 5 and 10 mg/kg in the ES+R (wolfberry glycopeptide) group.

(1) Effects on the Spleen Weight Index and Cerebral Cortex Weight Index in Mice

Seven days after administration, changes in the spleen weight index and cerebral cortex weight index are measured by a weighing method. The test results are shown in Table 16.

TABLE 16

Test results on weight of spleen and cerebral cortex in physical stressed mice

| tissue | Control | ES + R (saline) | ES + R (5 mg/Kg wolfberry glycopeptide) | ES + R (10 mg/Kg wolfberry glycopeptide) |
|---|---|---|---|---|
| spleen | 0.19 ± 0.03 | 0.15 ± 0.03** | 0.16 ± 0.03 | 0.18 ± 0.03 |
| Cerebral cortex | 0.18 ± 0.02 | 0.21 ± 0.01** | 0.22 ± 0.03 | 0.21 ± 0.03 |

**$p < 0.01$ Compared with control group

As shown in Table 16, after electroshock (ES) and γ-ray (R) irradiation, the spleen weight index of the mice in the ES+R (saline) group is significantly decreased and the cerebral cortex weight index is significantly increased compared with that in the control group. In the groups of mice administrated with wolfberry glycopeptide of Example 1, the spleen index and cerebral cortex weight index are not significantly different from those in the control group, indicating that the wolfberry glycopeptide protects the mice from the stimulation of physical stress.

(2) Effects on Mouse Lipid Peroxide (MDA)

Malondialdehyde (MDA) is a naturally produced lipid peroxide in the organisms and marker of oxidative stress. Thiobarbituric (TBA) method is used to determine $OD_{535-520\ nm}$ in the example. The index has a linear relationship with MDA contents in the serum and directly reflects the change in MDA. $OD_{535-520\ nm}$ of mice after stress is shown in Table 17:

TABLE 17

Testing Effects on stress-induced MDA in mouse tissues

| Group | $OD_{535-520\ nm}$ |
|---|---|
| Control group | 0.263 ± 0.008 |
| ES + R (saline) | 0.294 ± 0.026** |
| ES + R (5 mg/Kg of wolfberry glycopeptide) | 0.148 ± 0.008+++ |
| ES + R (10 mg/Kg of wolfberry glycopeptide) | 0.198 ± 0.015+++ |

**$p < 0.01$ Compared with control group;
+++$p < 0.001$ Compared with stress group As shown in Table 17, MDA of mice after stress is significantly increased, and the comparison of the wolfberry glycopeptide group and the ES+R (saline) group show that the wolfberry glycopeptide composition of the present invention significantly inhibits and reduces the production of MDA, therefore, has a significant protective effect on MDA damage.

Example 19. Wolfberry Glycopeptide Promotes Thymus Weight Gain in Older Mice

Thirteen month old mice with thymus atrophy are divided into control group and wolfberry glycopeptide group with 10 mice in each group. An equal volume of physiological saline solution is administered in the control group; the wolfberry glycopeptide of Example 1 is administered at a dose of 1.0 or 2.0 mg/Kg in the wolfberry glycopeptide group, and the administration method is injection. Seven days after the administration, the thymus weight of mice is measured, and the test results are shown in Table 18:

TABLE 18

Test results on thymus weight of older mice

| Groups | dose (mg/Kg · d) | Thymus index (mg/10 g) |
|---|---|---|
| Control | / | 2.4 ± 1.1 |
| Wolfberry Glycopeptide | 1.0 | 4.0 ± 0.8* |
| Wolfberry Glycopeptide | 2.0 | 6.0 ± 1.5** |

*$p < 0.05$ **$p < 0.01$ Compared with that in the control group

As shown in Table 18, the wolfberry glycopeptide composition of the present invention significantly improves growth of the atrophic thymus.

Example 20. Effect on Anti-$S_{180}$ Tumor

In this experiment, Kunming mice are divided into control group and wolfberry glycopeptide group with 10 mice for each. The next day after the mice are inoculated with $S_{180}$ tumor cells under armpits, an equal volume of normal saline is administrated in the control group; the wolfberry glycopeptide prepared according to the method of Example 1 of the present invention is administered by injection at a dose of 2, 5, or 10 mg/Kg for 7 consecutive days in the wolfberry glycopeptide group. The test results are shown in Table 19.

TABLE 19

Results of wolfberry glycopeptide in anti-$S_{180}$ sarcoma test

| Groups | dose (mg/Kg) | Average tumor weight g (X ± SD) | Tumor inhibitory rate (%) |
|---|---|---|---|
| Control | NS | 1.2 ± 0.5 | / |
| Wolfberry Glycopeptide | 2.0 | 1.1 ± 0.6 | / |
| Wolfberry Glycopeptide | 5.0 | 0.61 ± 0.3 | 49* |
| Wolfberry Glycopeptide | 10.0 | 0.50 ± 0.4 | 58* |

*$p < 0.05$ Compared with that in the control group

As shown in Table 19, the wolfberry glycopeptide at higher concentrations of 5.0 and 10.0 mg/kg had a significant anti-tumor effect.

Example 21. Effect on Tumor Suppressive Activity of Mouse Peritoneal Macrophages Effects of wolfberry glycopeptide on tumor suppressive activity of mouse peritoneal macrophages are examined in the example. *Corynebacterium Parvum* (CP) is an antitumor agent, and one of the important mechanisms of its anti-tumor effect is the activation of macrophages (M). Experimental female C57BL/6 mice are divided into 5 groups with 4 mice in each group. Four groups are wolfberry glycopeptide groups that are subcutaneously administered with 5-40 mg/Kg wolfberry glycopeptide of Example 1 on the first day; the next day, each mouse is intravenously administered with 250 m CP. On the seventh day, the peritoneal membrane of the mouse is washed with HBSS and peritoneal macrophages are collected. P815 or P388 cells are added to peritoneal macrophages and re-cultured for 24 hours. $^3$H-thymidine ($^3$H-TdR) incorporation method is used to determine target cells P815 and P388. The results are shown in Table 20:

TABLE 20

Test results of synergistic antitumor activity between glycopeptide and CP

| Groups | Incorporation of $^3$H-Tdr (cmp) | | Cell growth inhibition rate (%) | |
|---|---|---|---|---|
| | P815 | P388 | P815 | P388 |
| Tumor cell control group | 46290 ± 5452 | 5350 ± 385 | — | — |
| Mφ control group | 425 ± 245 | 809 ± 223 | — | — |
| CP | 35730 ± 1227* | 4876 ± 721 | 28.1* | 24.0 |
| CP + 5 mg/kg glycopeptide | 39194 ± 6160 | 3815 ± 423## | 16.3 | 43.8## |
| CP + 10 mg/kg glycopeptide | 20860 ± 3369# | 2842 ± 636# | 55.9# | 62.0# |
| CP + 20 mg/kg glycopeptide | 7726 ± 1437## | 2754 ± 182## | 85.3## | 63.6## |
| CP + 40 mg/kg glycopeptide | 12794 ± 1115## | 3622 ± 397## | 73.3## | 47.4## |

*p < 0.05 compared with tumor cell control group;
p < 0.05 ##p < 0.01 compared with CP group As shown in Table 20, the inhibition rates of the CP control group on the proliferation of target cells P815 and P388 are 28.1% and 24.0%, respectively. The synergistic effect of wolfberry glycopeptide at 20 mg/Kg is the most significant, and the inhibition rate is increased to 85.5% and 63.6%, respectively. Thus, the wolfberry glycopeptide composition of the present invention and CP have significant synergistic anti-tumor effects.

Example 22. Effect on Free Ca Concentration in Cardiomyocytes of Hypoxic Neonatal Mice SD neonatal mice are used for cardiomyocyte culture to establish a cardiomyocyte hypoxia model. Experimental mice are divided into three groups: (1) in the normal control group, cardiomyocytes are cultured in DMEM medium supplemented with 20% inactivated fetal bovine serum; (2) in the hypoxia model group, cells are subjected to hypoxia treatment (5% $CO_2$+95% $N_2$) for 6 hours; (3) in the wolfberry glycopeptide pretreatment groups: 25-100 μg/mL of wolfberry glycopeptide of Example 1 are added, respectively, and incubated for 12 hours, and then subjected to hypoxia treatment for 6 hours. Cell viability is measured by the MTT method, and the effect of wolfberry glycopeptide on the free calcium content in hypoxic cardiomyocytes is determined by laser scanning confocal microscopy system and Flou-3/AM fluorescence indicator labeling technique loaded with Fluo/AM fluorescence indicator.

Figure 15:
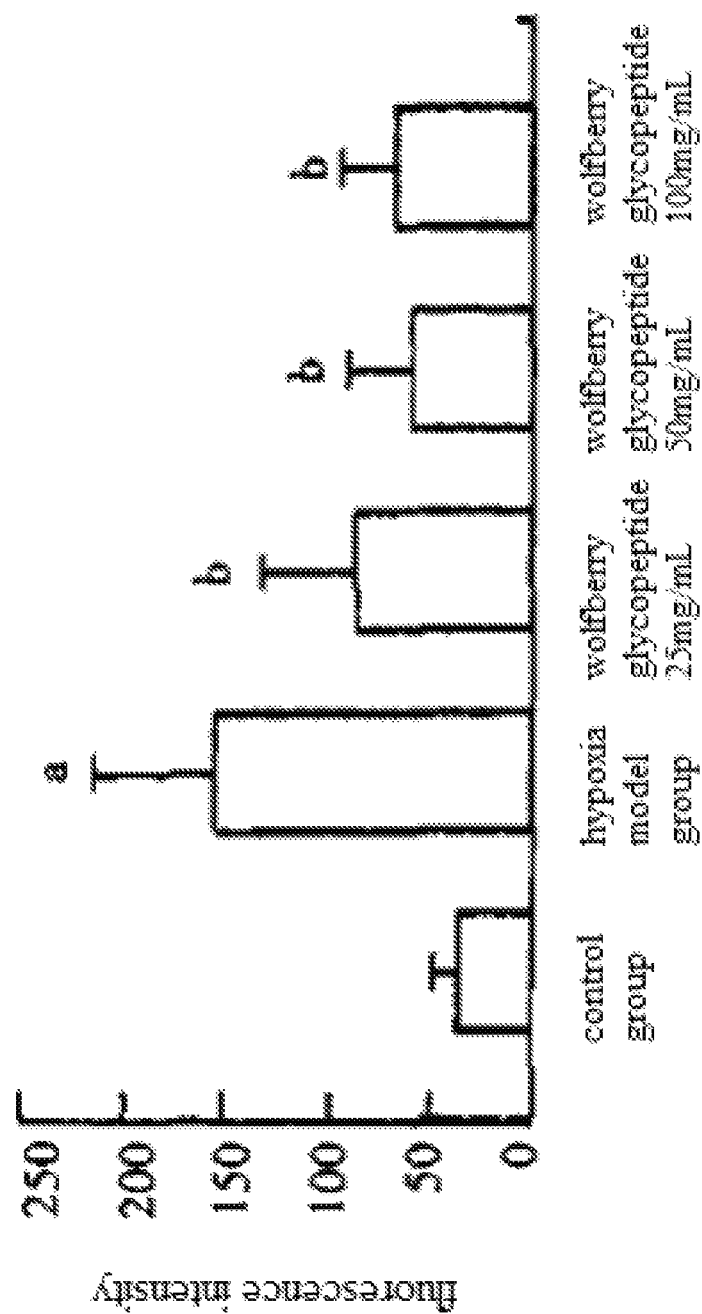
FIG. 15 shows the effect of the wolfberry glycopeptide composition of the present invention on the free calcium concentration of hypoxic cardiomyocytes as described in Example 22.

As shown in FIG. 15, the fluorescence density of $[Ca^{2+}]i$ is low in normal cells. After 6 hours of hypoxia, the fluorescence density of $[Ca^{2+}]i$ in cardiomyocytes of hypoxia group is significantly increased (156.76±55.39), compared with the normal control group (43.63±24.65), the difference is significant (P<0.01), indicating that 6 hours of hypoxia causes intracellular calcium overload in cardiomyocytes. After pretreatment with 25, 50 and 100 μg/mL wolfberry glycopeptide of Example 1, the fluorescence density of cardiomyocytes is significantly lower than that in the hypoxic model group (p<0.01), and the group pretreated with 50 μg/mL wolfberry glycopeptide shows the most significant effect (62.86±28.71, t=4.92, P<0.01) in reducing [Ca2+]i, indicating that the protection by the wolfberry glycopeptide composition of the present invention on hypoxic cardiomyocytes relates to reduction of intracellular calcium overload.

Example 23. Effect on Hypoxia and KCl-Induced Calcium Overload in Cardiomyocytes In the control group, cardiomyocytes of the SD rats are cultured in DMEM medium supplemented with 20% inactivated fetal bovine serum. The cellular free calcium content is determined by laser scanning confocal microscopy system and Flou-3/AM fluorescence indicator labeling technique.

Figures 16A, 16B:
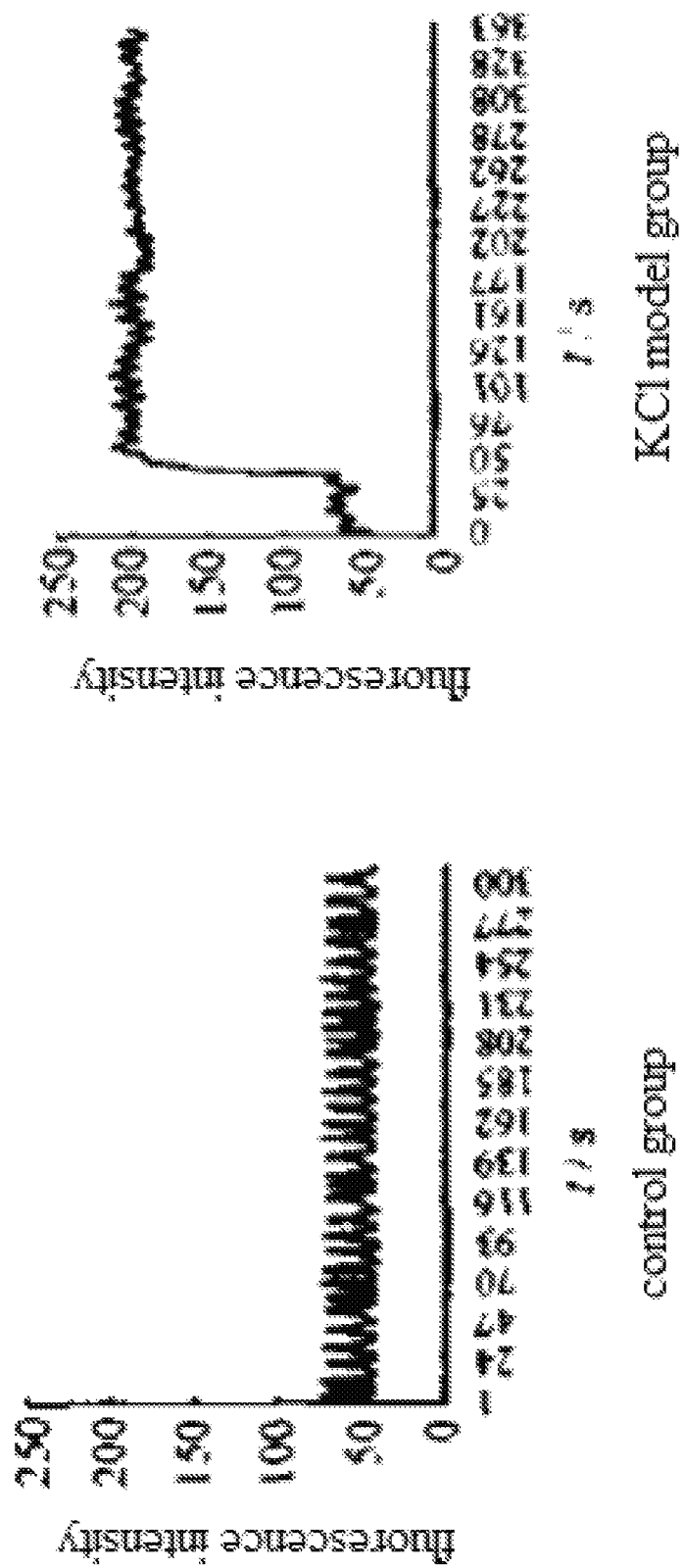
FIG. 16(a) shows the result in the control group.
FIG. 16(b) shows the result in the KCl model group.

In the KCl-induced cardiomyocyte $[Ca^{2+}]i$ group, the cardiomyocytes are loaded with dye liquor and the dynamic changes of $[Ca^{2+}]i$ in cardiomyocytes are continuous dynamic scanned under laser confocal microscopy. After recording a normal $[Ca^{2+}]i$ curve of cardiomyocytes, the final concentration of 60 mmol/L KCl solution is added. The fluorescence intensity curves of dynamic intracellular calcium in the control group and the KCl model group are shown in FIG. 16(a) and FIG. 16(b), respectively. As shown in FIG. 16(b), as compared with FIG. 16(a), the curve is rapidly increased and maintained at a high level in the KCl model group.

In the wolfberry glycopeptide pretreatment groups, cardiomyocytes are added with 25 μg/mL, 50 μg/mL, and 100 μg/mL wolfberry glycopeptide of Example 1, respectively, and incubated for 12 hours. The results of the fluorescent intensity curves at 25 μg/mL, 50 μg/mL, and 100 μg/mL are shown in FIGS. 16(c), 16(d), and 16(e), respectively. In these groups, the fluorescence intensity curve of $[Ca^{2+}]i$ in cardiomyocytes increase after stimulation with the equivalent dose of KCl. However, compared with the KCl model group as shown in FIG. 16(b), the amplitude of 25 μg/mL wolfberry glycopeptide group shown in FIG. 16(c) is significantly reduced, the curve of 50 μg/mL wolfberry glycopeptide group shown in FIG. 16(d) is already single peak, and the curve of 100 μg/mL wolfberry glycopeptide group shown in FIG. 16(e) is nearly flat. A dose-effect relationship is shown in the three groups.

In conclusion, the wolfberry glycopeptide composition of the present invention inhibit KCl-induced calcium overload in cardiomyocytes, suggesting that the protective effect of the wolfberry glycopeptide on cardiomyocyte injury may act on the L-type calcium channel and reduce intracellular calcium overload in cardiomyocytes.

Example 24. Test of Inhibition of Angiogenesis by Wolfberry Glycopeptide

During the metastasis of cancer cells, the cancer cells move along the blood vessel wall after falling off, and transferred from one organ to another. To complete the metastasis, the cancer cells must adhere to the vascular endothelial cells of another organ and generate new blood vessels to gain nutrients for growth. According to the principle, research on angiogenesis has become a research direction for exploring new anticancer drugs. The chick embryos are released into the culture medium with hatching egg, and the drugs are dropwise added to the chick chorioallantoic membrane (CAM) at the same time. After 48 hours of culture, the results are observed and recorded under a dissecting microscope.

In the example, the concentration of methyl cellulose in methyl cellulose blank group is 0.5%. The wolfberry glycopeptide groups have 6.25-100 μg/mL wolfberry glycopeptide of Example 1. The results on the inhibition of angiogenesis are shown in Table 21:

TABLE 21

Test results of inhibition of angiogenesis by wolfberry glycopeptide

| Wolfberry glycopeptide | Total number of blood vessels | Number of large blood vessels | Number of middle blood vessels | Number of small blood vessels |
|---|---|---|---|---|
| methyl cellulose blank group | 88.25 ± 9.39 | 3.00 ± 1.77 | 6.37 ± 1.06 | 78.87 ± 8.95 |
| 100 μg/mL | 75.28 ± 1.38 | 4.28 ± 1.38 | 5.43 ± 2.37 | 66.29 ± 16.14 |
| 50 μg/mL | 77.43 ± 7.23 | 4.57 ± 1.40 | 5.57 ± 0.97 | 67.42 ± 9.67 |
| 25 μg/mL | 70.40 ± 9.30* | 3.70 ± 2.45 | 4.00 ± 1.5* | 62.70 ± 9.67* |
| 12.5 μg/mL | 69.25 ± 14.51* | 4.63 ± 1.30 | 5.52 ± 1.93 | 59.12 ± 8.03* |
| 6.25 μg/mL | 71.33 ± 14.51* | 3.83 ± 2.93 | 5.5 ± 2.43 | 62.00 ± 13.58* |

*$p < 0.05$ Compared with that in methyl cellulose blank group

As shown in Table 21, after the wolfberry glycopeptide is fused with CAM, no vascular penetration is under the plate, the vasculars around the plate are fine and sparse, and the vessel diameter and density are significantly lower than those in the control group, showing the overall effect of inhibiting angiogenesis. The in vitro experiments shows that wolfberry glycopeptide has neovascularization inhibitory activity and potential tumor vascular targeting activity.

Example 25. Effect of Wolfberry Glycopeptide on the Cycle of Vascular Endothelial Cell Well-grown RF-6A cells are selected and incubated for 48 hours, and are randomly divided into five groups. The blank group is cultured in serum-free medium; the wolfberry glycopeptide groups are cultured in serum-free medium containing 5-40 μg/mL of wolfberry glycopeptide of Example 1. After 12 hours of culture, the percentage of each cell cycle is measured by flow cytometry. The results are shown in Table 22:

TABLE 22

Test results on the cycle of vascular endothelial cell

| Group | $G_0$-$G_1$ | $G_2$-M | S | $G_2/G_1$ |
|---|---|---|---|---|
| Blank control | 59.99 | 16.87 | 23.14 | 1.91 |
| 40 μg/mL of Wolfberry Glycopeptide | 80.30 | 7.88 | 11.81 | 1.89 |
| 20 μg/mL of Wolfberry Glycopeptide | 78.45 | 8.80 | 12.75 | 1.89 |
| 10 μg/mL of Wolfberry Glycopeptide | 73.20 | 12.96 | 13.85 | 1.92 |
| 5 μg/mL of Wolfberry Glycopeptide | 71.47 | 12.13 | 16.93 | 1.94 |

As shown in Table 22, as the concentration of wolfberry glycopeptide composition of the present invention increases in the wolfberry glycopeptides groups, the proportion of cells in the DNA synthetic and division phases decrease accordingly, while those in the G0-G1 phase (interphase and prophase) increase. Thus, the wolfberry glycopeptide composition of the present invention at 5-40 m/mL blocks the cycle of vascular endothelial cell in G0-G1 phase, thereby inhibiting of DNA synthesis and cell division and proliferation.

Example 26. Acute Toxicity Test of Oral Administration with Wolfberry Glycopeptide in Mice Fifty Kunming mice (weighed 20±1 g, half male and half female) are randomly divided into 5 groups with 10 mice in each group. The dosage of the administration group is determined according to the Bliss method. The distance between each administration group is 0.8, and the mice are observed for 7 days after administration.

The wolfberry glycopeptide of Example 1 is orally administrated to the mice and its effect is observed, including whether abnormal reactions such as systemic jitter, serious convulsion and death occur, as shown in Table 23:

TABLE 23

Results of acute toxicity test (oral administration) daily

| Dosage (mg/Kg) | number of the animal having positive reaction (death) daily | | | | | | | | Death rate (%) |
|---|---|---|---|---|---|---|---|---|---|
| | immediately | 1st | 2nd | 3rd | 4th | 5th | 6th | 7th | |
| 524.0 | 0 | 1 | 0 | 0 | 0 | 0 | 0 | 0 | 10.0 |
| 655.0 | 0 | 3 | 1 | 0 | 0 | 0 | 0 | 0 | 40.0 |
| 819.0 | 0 | 5 | 2 | 0 | 0 | 0 | 0 | 0 | 70.0 |
| 1024.0 | 0 | 6 | 2 | 1 | 0 | 0 | 0 | 0 | 90.0 |
| 1280.0 | 0 | 8 | 2 | / | / | / | / | / | 100.0 |

The $LD_{50}$ of the wolfberry glycopeptide is calculated to be 713.5 mg/Kg with a confidence interval of 619.8-804.9 mg/Kg.

Example 27. Clinical Observation of Wolfberry Glycopeptide in the Treatment of Fatty Liver Thirty-eight (38) patients with fatty liver are selected, including 32 males and 6 females, according to the following criteria: (1) fatty liver changes are shown by B-ultrasound; (2) the patients are associated with fatty liver-related diseases such as obesity and hyperlipidemia; (3) ALT is increased 2-3 folds and blood lipid is increased.

The patients orally take 30 mg wolfberry glycopeptide of Example 1 twice daily for 3 months, and other liver protecting drugs are used as usual.

Results on ALT, AST, TP, ALB, TB, DB, T-chol, TG, LDL, HDL, B-ultrasound, and clinical symptoms are observed and recorded. The changes after the treatment in the patients are shown in Table 24:

TABLE 24

Clinical results in the treatment of fatty liver

| cases | | Alt | AST | TB | DB | TG |
|---|---|---|---|---|---|---|
| 38 | Before | 83.71 ± 57.69 | 56.63 ± 33.97 | 14.75 ± 5.01 | 4.51 ± 1.08 | 2.46 ± 1.36 |
| | 3 months later | 54.12 ± 26.26 | 46.88 ± 44.63 | 13.59 ± 4.1 | 34.55 ± 1.21 | 2.09 ± 1.21 |
| | P value | <0.05 | >0.05 | >0.05 | >0.05 | <0.05 |

As shown in Table 24, the patients treated with the wolfberry glycopeptide show significant decrease in ALT and TG (p<0.05), and there is no significant difference among the other three indicators. Clinical symptoms of the patients after treatment are improved to different extents. The B-ultrasound results show that two patients have a reduced degree of fatty liver. Thus, the treatment of fatty liver patients with glycopeptide of present invention improves the B-ultrasound performance of liver in some patients, and the effects of enzyme-lowering and lipid-lowering are obvious.

Those skilled in the art may make changes or modifications based on the disclosure of the subject application without departing from the scope of the present invention.

We claim:

1. A method for preparing a glycopeptide composition, comprising:
   (a) soaking fruit of wolfberry in water and centrifuging to remove precipitated solids to obtain a first extract solution;
   (b) heating the first extract solution to provide a flocculation in the first extract solution, and centrifuging the first extract solution to remove the flocculation to obtain a second extract solution, wherein the second extract solution has a light transmittance at 50% or higher at 400 nm; and
   (c) treating the second extract solution with an ultrafiltration membrane, obtaining a cut-off solution with a molecular weight cutoff of the ultrafiltration membrane, concentrating, and drying the cut-off solution to obtain a glycopeptide composition,
   wherein the flocculation is formed by agglomerating insoluble substances in the first extract solution into precipitates, the molecular weight cutoff of the ultrafiltration membrane is in a range of 1000 Da to 2000 Da, and each of the steps (1) to (3) is conducted in water only.

2. The method of claim 1, wherein the fruit wolfberry is soaked in water at a temperature in a range of 10° C. to 35° C. for 2 hours to 10 hours.

3. The method of claim 1, wherein the first extract solution is heated at a temperature in a range of 45° C. to 70° C. for 0.5 hour to 5 hours to form the flocculation.

4. The method of claim 1, wherein the mass ratio of the fruit of wolfberry to water for soaking in step (a) is 1:1 to 1:15.

5. The method of claim 4, wherein the fruit of wolfberry is dried fruit, and the mass ratio of the dried fruit to the amount of the water for soaking is 1:5 to 1:15.

6. The method of claim 4, wherein the fruit of wolfberry is fresh fruit, and the mass ratio of the fresh fruit to the amount of the water for soaking is 1:1 to 1:3.

7. The method of claim 1, wherein centrifuging to obtain the first extract solution is at a centrifugal speed of 1000 rpm to 4000 rpm for 10 seconds to 1 minute.

8. The method claim 1, wherein the light transmittance of the second extract solution is at 60% or more at 400 nm.

9. The method of claim 1, wherein the first extract solution is heated to a temperature in a range of 45° C. to 70° C. for a time period of 0.5 hour to 5 hours, and centrifuged at a centrifugal speed of 6000 rpm to 16000 rpm for 5 seconds to 5 minutes.

10. The method of claim 1, wherein the cut-off solution is dried by freeze drying, spray drying, or a combination thereof, to obtain the glycopeptide composition.

11. The method of claim 1, further comprising:
   continuously providing water to the cut-off solution during ultrafiltration in step (c); and
   monitoring electrical conductivity and sugar degree of the cut-off solution; wherein the cut-off solution is collected when the electrical conductivity of the cut-off solution is below 1000us/cm and the sugar degree is below 1.2.

* * * * *